United States Patent [19]

Soyka et al.

[11] Patent Number: 5,482,948

[45] Date of Patent: Jan. 9, 1996

[54] PYRIDYL DERIVATIVES AND PHARMACEUTICAL COMPOSITIONS COMPRISING THESE COMPOUNDS

[75] Inventors: Rainer Soyka; Thomas Müller; Johannes Weisenberger, all of Biberach, Germany

[73] Assignee: Dr. Karl Thomae GmbH, Biberach an der Riss, Germany

[21] Appl. No.: 270,615

[22] Filed: Jul. 5, 1994

Related U.S. Application Data

[63] Continuation of Ser. No. 989,681, Dec. 14, 1992, abandoned.

[30] Foreign Application Priority Data

Dec. 14, 1991 [DE] Germany .................. 41 41 377.6
May 21, 1992 [DE] Germany .................. 42 16 829.5
May 18, 1992 [DE] Germany .................. 42 16 364.1

[51] Int. Cl.$^6$ .................. A61K 31/44; C07D 401/10; C07D 213/16; C07D 211/14
[52] U.S. Cl. .................. 514/318; 514/332; 514/343; 514/357; 546/194; 546/264; 546/281; 546/330; 546/333
[58] Field of Search .................. 546/194, 264, 546/281, 330, 333; 514/318, 332, 343, 357

[56] References Cited

FOREIGN PATENT DOCUMENTS 0397044 11/1990 European Pat. Off. .
0405391 1/1991 European Pat. Off. .

*Primary Examiner*—Marianne M. Cintins
*Assistant Examiner*—Phyllis G. Spirack
*Attorney, Agent, or Firm*—R. P. Raymond; A. R. Stempel; M-E. M. Devlin

[57] ABSTRACT

This invention relates to pyridyl derivatives of the formula

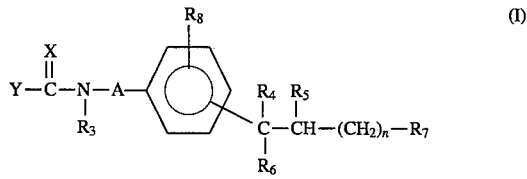

(I)

wherein

X, Y, A, n and $R_3$ to $R_8$ are defined hereinbelow, the enantiomers thereof, the cis- and trans-isomers thereof, which have antithrombotic pharmaceutical activity.

45 Claims, No Drawings

PYRIDYL DERIVATIVES AND PHARMACEUTICAL COMPOSITIONS COMPRISING THESE COMPOUNDS

This is a continuation of application Ser. No. 07/989,681, filed Dec. 14, 1992 now abandoned.

The present invention relates to new pyridyl derivatives of the general formula

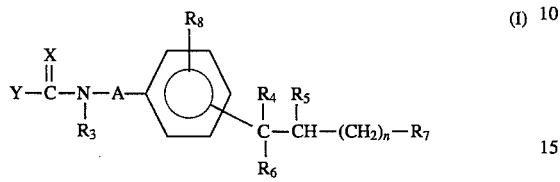

wherein n represents the number 2, 3, 4 or 5,

A denotes a carbon-nitrogen bond or a straight-chained $C_{1-4}$-alkylene group optionally substituted by one or two alkyl groups, X denotes a nitromethylene group, a cyanomethylene group optionally substituted by an $R_9$ group, or a group of the formula $=N-R_{10}$, wherein $R_9$ has the meanings given for $R_7$ hereinafter with the exception of the tetrazolyl group and $R_{10}$ denotes a cyano, alkanesulphonyl, phenylsulphonyl, phenylalkanesulphonyl, aminosulphonyl, alkylaminosulphonyl, dialkylaminosulphonyl, phenylcarbonyl, aminocarbonyl, alkylaminocarbonyl or dialkylaminocarbonyl group, Y denotes an alkoxy, phenoxy, alkylthio or phenylthio group or a group of the formula $-R_1NR_2$ (wherein $R_1$ denotes a hydrogen atom, a straight-chained or branched $C_{1-10}$-alkyl group which may be substituted in the 2-, 3- or 4-position by a hydroxy, amino, alkylamino or dialkylamino group, a $C_{1-4}$-alkyl group which is substituted by a phenyl or pyridyl group and which may additionally be substituted in the 2-, 3- or 4-position by a hydroxy group, a $C_{3-4}$-cycloalkyl group, a $C_{5-8}$-cycloalkyl group in which an ethylene bridge may be replaced by an o-phenylene group, a $C_{6-8}$-bicycloalkyl group optionally substituted by 1, 2 or 3 alkyl groups, or an adamantyl, alkoxy or trimethylsilylalkyl group, $R_2$ denotes a hydrogen atom or a straight-chained alkyl group or $R_1$ and $R_2$ together with the nitrogen atom between them denote a cyclic $C_{4-6}$-alkyleneimino group which may be substituted by one or two alkyl groups or by a phenyl group and wherein additionally an ethylene bridge in the 3,4-position may be replaced by an o-phenylene group, they denote a morpholino group or a piperazino group optionally substituted in the 4-position by a $C_{1-3}$-alkyl group or by a phenyl group), $R_3$ denotes a hydrogen atom or a $C_{1-3}$-alkyl group, $R_4$ and $R_5$ each denote a hydrogen atom or together represent a carbon-carbon bond, $R_6$ denotes a pyridyl group optionally substituted in the 3- or 4-position by an alkyl group, $R_7$ denotes a cyano, tetrazolyl, aminocarbonyl, alkylaminocarbonyl or dialkylaminocarbonyl group, a group which may be metabolically converted into a carboxy group in vivo or, if Y denotes an $R_1NR_2$— group, $R_7$ may represent a carboxy group, $R_8$ denotes a hydrogen, fluorine, chlorine, bromine or iodine atom or an alkyl, alkoxy or trifluoromethyl group, whilst all the above-mentioned alkyl and alkoxy moieties, unless otherwise stated, may contain one to three carbon atoms, and all the above-mentioned phenyl nuclei, unless otherwise stated, may be mono- or disubstituted by fluorine, chlorine or bromine atoms or by alkyl, hydroxy, alkoxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylamino-sulphonyl groups, and the substituents may be identical or different, the enantiomers thereof, the cis- and trans-isomers thereof (where $R_4$ and $R_5$ together denote a carbon-carbon bond) and the salts thereof.

By the term "a group which is metabolically converted into a carboxy group in vivo" used above is meant, for example, the esters thereof of formulae

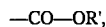

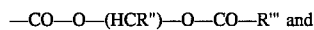

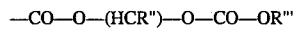

wherein

R' denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R" denotes a hydrogen atom or a methyl group and R'" denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group.

The compounds of general formula I above wherein Y denotes an alkoxy, phenoxy, alkylthio or phenylthio group are intermediate products for preparing the compounds of general formula I wherein Y denotes an $R_1NR_2$— group, and the compounds of the above general formula I wherein $R_7$ denotes a cyano group, are intermediate products for preparing compounds of general formula I wherein $R_7$ represents a tetrazolyl group.

The compounds of general formula I wherein Y denotes an $R_1NR_2$— group have, in particular, antithrombotic effects and furthermore the new compounds are also thromboxane antagonists (TRA) and thromboxane synthesis inhibitors (TSH) and thus also inhibit the effects mediated by thromboxane. Moreover, they also have an effect on $PGE_2$ production in the lungs and on the $PGD_2$, $PGE_2$ and $PGF_{2\alpha}$ production in human thrombocytes.

The present invention thus relates to the new intermediate products of general formula I above, the enantiomers thereof, the cis- and trans-isomers thereof (where $R_4$ and $R_5$ together denote a carbon-carbon bond), and the salts thereof, as well as to the new compounds of formula I above which have valuable pharmacological properties, the salts thereof with inorganic or organic acids or bases, more particularly for pharmaceutical use the physiologically acceptable salts thereof, pharmaceutical compositions containing these compounds and processes for preparing them.

As examples of the meanings covered by the definitions of the groups hereinbefore:

A may represent a methylene, ethylene, n-propylene, n-butylene, α-methyl-ethylene, α-methyl-n-propylene, α-ethyl-n-propylene, α-n-propyl-n-propylene, α,α-dimethyl-n-propylene, α,α-diethyl-n-propylene, β-methyl-n-propylene, γ-methyl-n-propylene, α-methyl-n- butylene or α,α-dimethyl-n-butylene group, the indices relating to the phenyl group, $R_1$ may represent a hydrogen atom, a methyl, ethyl, n-propyl, isopropyl, n-butyl, isobutyl, tert.butyl, 1,1,3,3-tetramethylbutyl, n-pentyl, neopentyl, n-hexyl, n-heptyl, n-octyl, n-nonyl, n-decyl, benzyl, 2-phenylethyl, 3-phenylpropyl, pyridylmethyl, 2-pyridylethyl, 3-pyridylpropyl, 2-hydroxy-2-phenylethyl, 2-hydroxy-1-methyl-2-phenylethyl, 2-hydroxy-1,1-dimethylethyl, cyclopropyl, cyclobutyl, cyclopentyl, cyclohexyl, cycloheptyl, cyclooctyl, indan-1-yl, indan-2-yl, 1,2,3,4-tetrahydronaphth-1-yl, 1,2,3,4-tetrahydronaphth-2-yl, 2-hydroxyethyl, 3-hydroxy-n-propyl, 4-hydroxy-n-butyl, 2-hydroxy-isopropyl, hydroxy-tert.butyl, exo-norbornyl, endo-norbornyl, 1-adamantyl, 2-adamantyl, methoxy, ethoxy, n-propoxy, isopropoxy, 2-aminoethyl, 3-amino-propyl, 4-aminobutyl, 2-methylamino-ethyl, 3-methylamino-propyl, 4-methylamino-butyl, 2-ethylamino-ethyl, 3-ethylamino-propyl, 4-ethylamino-butyl, 2-n-propylamino-ethyl, 3-n-propylamino-propyl, 4-n-propylamino-butyl, 2-isopropylamino-ethyl, 3-isopropylamino-propyl, 4-isopropylamino-butyl, 2-dimethylamino-ethyl, 3-dimethylamino-propyl, 4-dimethylaminobutyl, 2-diethylamino-ethyl, 3-diethylamino-propyl, 4-diethylamino-butyl, 2-di-n-propylamino-ethyl, 3-di-n-propylamino-propyl, 4-di-n-propylamino-butyl, trimethylsilylmethyl, 2-trimethylsilylethyl or 3-trimethylsilylpropyl group, $R_2$ may represent hydrogen or a methyl, ethyl, n-propyl or isopropyl group, $R_1$ and $R_2$ together with the nitrogen atom between them may denote a pyrrolidino, piperidino, hexamethyleneimino, 3-methyl-piperidino, 3,3-dimethyl-piperidino, 4-phenylpiperidino, morpholino, piperazino, N-methyl-piperazino, N-ethyl-piperazino, N-propyl-piperazino, N-phenyl-piperazino, isoindolin-2-yl, 1,2,3,4-tetrahydroisoquinolin-2-yl or 1,3,4,5-tetrahydro-2H-benzazepin-2-yl or 1,2,4,5-tetrahydro- 3H-benzazepin-3-yl, $R_3$ may denote a hydrogen atom or a methyl, ethyl, n-propyl or isopropyl group, $R_6$ may denote a 3-methylpyridyl-(2)-, 3-ethylpyridyl-(2)-, 3-n-propylpyridyl-(2)-, 3-isopropylpyridyl-(2)-, 4-methylpyridyl-(2)-, 4-ethylpyridyl-(2)-, 4-n-propylpyridyl-(2)-, 4-isopropylpyridyl-(2)-, 5-methylpyridyl-(2)-, 5-ethylpyridyl-(2)-, 5-n-propylpyridyl-(2)-, 5-isopropylpyridyl-(2)-, 4-methylpyridyl-(3)-, 4-ethylpyridyl-(3)-, 4-n-propylpyridyl-(3)-, 4-isopropylpyridyl-(3)-, 5-methylpyridyl-(3)-, 5-ethylpyridyl-(3)-, 5-n-propylpyridyl-(3)-, 5-isopropylpyridyl-(3)-, 3-methylpyridyl-(4)-, 3-ethylpyridyl-(4)-, 3-n-propylpyridyl-(4)-, 3-isopropylpyridyl-(4)-, $R_7$ may denote a cyano, 1H-tetrazolyl-, 2H-tetrazolyl-, hydroxycarbonyl, methoxycarbonyl, ethoxycarbonyl, n-propyloxycarbonyl, isopropyloxycarbonyl, n-butyloxycarbonyl, isobutyloxycarbonyl, tert.butyloxycarbonyl, n-pentyloxycarbonyl, isoamyloxycarbonyl, n-hexyloxycarbonyl, cyclopentyloxycarbonyl, cyclohexyloxycarbonyl, benzyloxycarbonyl, 1-phenylethyloxycarbonyl, 2-phenylethyloxycarbonyl, 3-phenylpropyloxycarbonyl, methoxymethoxycarbonyl, cinnamyloxycarbonyl, acetoxymethoxycarbonyl, propionyloxymethoxycarbonyl, n-butyryloxymethoxycarbonyl, isobutyryloxymethoxycarbonyl, n-pentanoyloxymethoxycarbonyl, isopentanoyloxymethoxycarbonyl, pivaloyloxymethoxy-carbonyl, n-hexanoyloxymethoxycarbonyl, cyclopentanoyloxymethoxycarbonyl, cyclohexanoyloxymethoxycarbonyl, phenylacetoxymethoxycarbonyl, 1-phenylpropionyloxymethoxycarbonyl, 2-phenylpropionyloxymethoxycarbonyl, 3-phenylbutyryloxymethoxycarbonyl, benzoyloxymethoxycarbonyl, 1-acetoxyethoxycarbonyl, 1-propionyloxyethoxycarbonyl, 1-n-butyryloxyethoxycarbonyl, 1-isobutyryloxy-ethoxycarbonyl, 1-n-pentanoyloxyethoxycarbonyl, 1-isopentanoyloxyethoxycarbonyl, 1-pivaloyloxy-ethoxycarbonyl, 1-n-hexanoyloxyethoxycarbonyl, 1-cyclopentanoyloxyethoxycarbonyl, 1-cyclohexanoyloxyethoxycarbonyl, 1-phenylacetoxyethoxycarbonyl, 1-(1-phenylpropionyloxy)-ethoxycarbonyl, 1-(2-phenylpropionyloxy)-ethoxycarbonyl, 1-(3-phenylbutyryloxy)-ethoxycarbonyl, 1-benzoyloxy-ethoxycarbonyl, methoxycarbonyloxymethoxycarbonyl, ethoxycarbonyloxymethoxycarbonyl, n-propyloxycarbonyloxymethoxycarbonyl, isopropyloxycarbonyloxymethoxycarbonyl, n-butyloxycarbonyloxymethoxycarbonyl, isobutyloxycarbonyloxymethoxycarbonyl, tert.butyloxycarbonyloxymethoxycarbonyl, n-pentyloxycarbonyloxymethoxycarbonyl, isoamyloxycarbonyloxymethoxycarbonyl, n-hexyloxycarbonyloxymethoxycarbonyl, cyclopentyloxycarbonyloxymethoxycarbonyl, cyclohexyloxycarbonyloxymethoxycarbonyl, benzyloxycarbonyloxymethoxycarbonyl, 1-phenylethoxycarbonyloxy-methoxycarbonyl, 2-phenylethoxycarbonyloxy-methoxycarbonyl, 3-phenylpropyloxycarbonyloxy-methoxycarbonyl, cinnamyloxycarbonyloxymethoxycarbonyl, 1-(methoxycarbonyloxy)-ethoxycarbonyl, 1-(ethoxycarbonyloxy)ethoxycarbonyl, 1-(n-propyloxycarbonyloxy)-ethoxycarbonyl, 1-(isopropyloxycarbonyloxy)-ethoxycarbonyl, 1-(n-butyloxycarbonyloxy)-ethoxycarbonyl, 1-(isobutyloxycarbonyloxy)-ethoxycarbonyl, 1-(tert.butyloxycarbonyloxy)-ethoxycarbonyl, 1-(n-pentyloxycarbonyloxy)ethoxycarbonyl, 1-(isoamyloxycarbonyloxy)-ethoxycarbonyl, 1-(n-hexyloxycarbonyloxy)-ethoxycarbonyl, 1-(cyclopentyloxycarbonyloxy)-ethoxycarbonyl, 1-(cyclohexyloxycarbonyloxy)-ethoxycarbonyl, cyclopentylcarbonyloxymethoxycarbonyl, (1,3-dioxa-2-oxo-4-methyl-cyclopenten-5-yl)-methoxycarbonyl, 1-(benzyloxycarbonyloxy)-ethoxycarbonyl, 1-(1-phenylethoxycarbonyloxy)-ethoxycarbonyl, 1-(2-phenylethoxycarbonyloxy)-ethoxycarbonyl, 1-(3-phenylpropyloxycarbonyloxy)-ethoxycarbonyl, 1-(cinnamyloxycarbonyloxy)-ethoxycarbonyl, aminocarbonyl, methylaminocarbonyl, ethylaminocarbonyl, n-propylaminocarbonyl, isopropylaminocarbonyl, dimethylaminocarbonyl, diethylaminocarbonyl, di-n-propylaminocarbonyl or diisopropylaminocarbonyl group, $R_8$ may denote a hydrogen, fluorine, chlorine, bromine or iodine atom or a methyl, ethyl, n-propyl, isopropyl, methoxy, ethoxy, n-propoxy, isopropoxy or trifluoromethyl group, $R_9$ may have the meanings given for $R_7$ hereinbefore with the exception of the tetrazolyl group, and $R_{10}$ may denote a cyano, methanesulphonyl, ethanesulphonyl, propanesulphonyl, isopropanesulphonyl, phenylsulphonyl, phenylmethanesulphonyl, 2-phenylethanesulphonyl, 3-phenylpropanesulphonyl, aminosulphonyl, methylamino-sulphonyl, ethylaminosulphonyl, isopropylaminosulphonyl, dimethylaminosulphonyl, diethylaminosulphonyl, di-n-propylaminosulphonyl, N-ethyl-methylaminosulphonyl, phenylcarbonyl, aminocarbonyl, methylaminocarbonyl, ethylaminocarbonyl, isopropylaminocarbonyl, dimethylaminocarbonyl, diethylaminocarbonyl, di-n-propylaminocarbonyl or N-ethyl-methylaminocarbonyl group.

However, preferred compounds of formula I above are those wherein n denotes the number 2, 3, 4 or 5, A is a bond or an ethylene group, X is a nitromethylene group, a cyanomethylene group optionally substituted by an $R_9$ group, or a group of the formula $=N-R_{10}$, wherein $R_9$ has the meanings given for $R_7$ hereinafter with the exception of the tetrazolyl group and $R_{10}$ denotes a cyano, phenylsulphonyl or alkanesulphonyl group, Y denotes a phenoxy or methylthio group or an $R_1NR_2-$ group (wherein $R_1$ is a hydrogen atom, a straight-chained or branched $C_{1-8}$-alkyl group which may be substituted in the 2-, 3- or 4-position by a hydroxy or dimethylamino group, a $C_14$-alkyl group which is substituted by a phenyl or pyridyl group and may additionally be substituted in the 2-, 3- or 4-position by a hydroxy group, a $C_{3-8}$-cycloalkyl group, a methoxy, trimethylsilylmethyl or indan-2-yl group or a bicycloheptyl group optionally substituted by 1, 2 or 3 alkyl groups and $R_2$ is a hydrogen atom or a methyl group or $R_1$ and $R_2$ together with the nitrogen atom between them denote a piperidino group which may be substituted by one or two methyl groups or by a phenyl group and wherein additionally an ethylene bridge in the 3,4-position may be replaced by an o-phenylene group, or they denote a morpholino group or a piperazino group substituted in the 4-position by a phenyl group), $R_3$ denotes a hydrogen atom or a methyl group, $R_4$ and $R_5$ each denote a hydrogen atom or together represent another carbon-carbon bond, $R_6$ denotes a 3-pyridyl or 4-pyridyl group and $R_7$ denotes a cyano, carboxy, tetrazolyl, alkoxycarbonyl, aminocarbonyl, alkylaminocarbonyl or dialkylaminocarbonyl group each having 1 to 3 carbon atoms in the alkoxy and alkyl moieties, $R_8$ denotes a hydrogen, fluorine, chlorine or bromine atom or an alkyl, alkoxy or trifluoromethyl group, whilst unless otherwise stated all the above-mentioned alkyl and alkoxy moieties may contain one to three carbon atoms, the enantiomers thereof, the cis- and trans-isomers thereof (where $R_4$ and $R_5$ together denote a carbon-carbon bond) and the salts thereof.

However, particularly preferred compounds of formula I are those wherein n denotes the number 3, A denotes a bond or an ethylene group, X denotes a group of the formula $=N-R_{10}$ (wherein $R_{10}$ is a cyano or phenylsulphonyl group) or a dicyanomethylene group, Y is an $R_1NR_2-$ group (wherein $R_1$ is a straight-chained or branched $C_{1-8}$-alkyl group, a $C_{3-8}$-cycloalkyl group or an exonorbornyl-(2) group and $R_2$ is a hydrogen atom), $R_3$ is a hydrogen atom, $R_4$ and $R_5$ each represent a hydrogen atom or together denote a carbon-carbon bond, $R_6$ is a 3-pyridyl group and $R_7$ denotes a carboxy or alkoxycarbonyl group having a total of 2 to 4 carbon atoms, $R_8$ is a hydrogen, chlorine or bromine atom or a methyl or trifluoromethyl group, the enantiomers thereof, the cis- and trans-isomers thereof and the salts thereof.

According to the invention the new compounds are obtained by the following methods:

a) In order to prepare compounds of general formula I wherein Y denotes an alkoxy, phenoxy, alkylthio or phenylthio group:

Reacting a compound of general formula

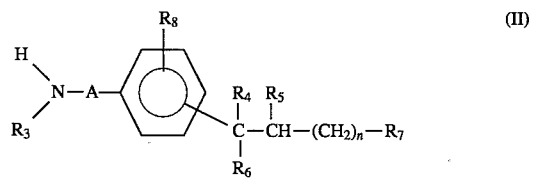

wherein

A, n and $R_3$ to $R_8$ are as hereinbefore defined, with a compound of general formula

$(Y')_2C=X$         (III)

wherein

X is as hereinbefore defined and

Y' denotes an alkoxy, phenoxy, alkylthio or phenylthio group.

The reaction is preferably carried out in a solvent such as methanol, ethanol, isopropanol, dioxane, tetrahydrofuran or chloroform, optionally in the presence of an acid binding agent such as potassium carbonate, triethylamine or pyridine, whilst the latter two may also be used as solvents, appropriately at temperatures between 0° and 50° C. but preferably at ambient temperature.

b) In order to prepare compounds of general formula I wherein Y represents an $R_1NR_2-$ group:

Reacting a compound of general formula

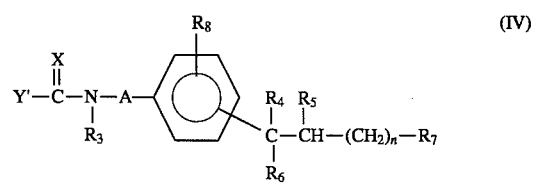

wherein

A, X, n and $R_3$ to $R_8$ are as hereinbefore defined and

Y' denotes an alkoxy, phenoxy, alkylthio or phenylthio group, with an amine of general formula

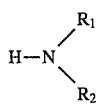 (V)

wherein $R_1$ and $R_2$ are as hereinbefore defined.

The reaction is preferably carried out in a solvent such as ethanol, isopropanol, tetrahydrofuran, dioxane or benzene or in an excess of the amine of general formula V used, optionally in a pressure vessel and optionally in the presence of a base such as sodium carbonate, potassium carbonate, triethylamine or pyridine at temperatures between 0° and 125° C., preferably at temperatures between 50° and 100° C.

c) In order to prepare compounds of general formula I wherein Y denotes an $R_1NR_2$— group and $R_7$ denotes a carboxy group:

Cleaving a protective group from a compound of general formula

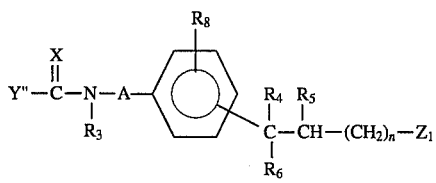 (VI)

wherein $R_3$ to $R_6$, $R_8$, A, X and n are as hereinbefore defined,

Y" denotes an $R_1NR_2$— group, wherein $R_1$ and $R_2$ are as hereinbefore defined, and $Z_1$ denotes a group which may be converted into a carboxy group by hydrolysis, thermolysis or hydrogenolysis.

Examples of hydrolysable groups include the functional derivatives of the carboxy group such as the unsubstituted or substituted amides, esters, thioesters, orthoesters, iminoethers, amidines or anhydrides thereof, the nitrile group, ether groups such as the methoxy, ethoxy, tert.butoxy or benzyloxy group or lactones and examples of thermolytically cleavable groups include esters with tertiary alcohols, e.g. the tert.butylester and examples of hydrogenolytically cleavable groups include aralkyl groups, e.g. the benzyl group.

The hydrolysis is conveniently carried out either in the presence of an acid such as hydrochloric acid, sulphuric acid, phosphoric acid or trichloroacetic acid or in the presence of a base such as sodium hydroxide or potassium hydroxide in a suitable solvent such as water, water/methanol, ethanol, water/ethanol, water/isopropanol or water/dioxane at temperatures between −10° and 120° C., e.g. at temperatures between ambient temperature and the boiling temperature of the reaction mixture.

If for example a compound of formula VI contains a nitrile or aminocarbonyl group, these groups may preferably be converted into the carboxy group using 100% phosphoric acid at temperatures between 100° and 180° C., preferably at temperatures between 120° and 160° C., or with a nitrite, e.g. sodium nitrite, in the presence of an acid such as sulphuric acid, the latter appropriately being simultaneously used as a solvent, at temperatures between 0° and 50° C.

If for example a compound of formula VI contains an acid amide group such as the diethylaminocarbonyl or piperidinocarbonyl group, this group may preferably be hydrolytically converted into a carboxy group in the presence of an acid such as hydrochloric acid, sulphuric acid, phosphoric acid or trichloroacetic acid or in the presence of a base such as sodium hydroxide or potassium hydroxide in a suitable solvent such as water, water/methanol, ethanol, water/ethanol, water/isopropanol or water/dioxane at temperatures between −10° and 120° C., e.g. at temperatures between ambient temperature and the boiling temperature of the reaction mixture.

If for example a compound of formula VI contains a tert.butyloxycarbonyl group, the tert.butyl group may also be thermally cleaved, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° and 100° C.

If for example a compound of formula VI contains a benzyloxy or benzyloxycarbonyl group, the benzyl group may also be hydrogenolytically cleaved in the presence of a hydrogenation catalyst such as palladium/charcoal in a suitable solvent such as methanol, ethanol, methanol/water, ethanol/water, glacial acetic acid, ethyl acetate, dioxane or dimethylformamide, preferably at temperatures between 0° and 50° C., e.g. at ambient temperature under a hydrogen pressure of from 1 to 5 bar. During the hydrogenolysis, a halogen containing compound may simultaneously be dehalogenated and any double bond present may be hydrogenated.

d) In order to prepare compounds of general formula I wherein $R_4$ and $R_5$ each represent a hydrogen atom:

Hydrogenating a compound of general formula

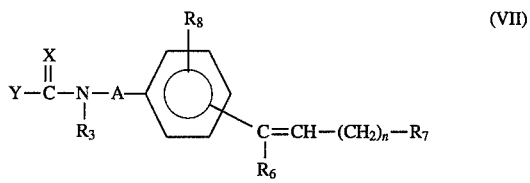 (VII)

wherein

A, X, Y, n, $R_3$ and $R_6$ to $R_8$ are as hereinbefore defined.

The hydrogenation is carried out in a suitable solvent such as methanol, ethanol, dioxane, ethyl acetate or glacial acetic acid with catalytically activated hydrogen, e.g. with hydrogen in the presence of a hydrogenation catalyst such as Raney nickel, palladium, palladium/charcoal, platinum or platinum/charcoal and under a hydrogen pressure of from 1 to 5 bar, or with nascent hydrogen, e.g. in the presence of iron/hydrochloric acid, zinc/glacial acetic acid, tin(II)chloride/hydrochloric acid or iron(II)sulphate/sulphuric acid, at temperatures between 0° and 50° C., preferably at ambient temperature. The catalytic hydrogenation may, however, also be carried out stereoselectively in the presence of a suitable catalyst.

e) In order to prepare compounds of general formula I wherein X has the meanings given for X hereinbefore, with the exception of the cyano-containing groups, and $R_7$ denotes a tetrazolyl group:

Reacting a compound of general formula

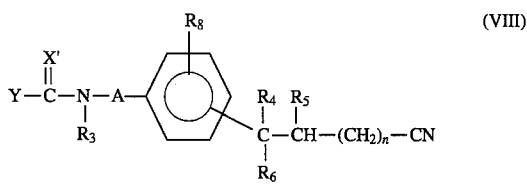

(VIII)

wherein

A, n, Y, $R_3$ to $R_6$ and $R_8$ are as hereinbefore defined and X' has the meanings given for X hereinbefore with the exception of the cyano-containing groups, with hydrazoic acid or the salts thereof.

The reaction is preferably carried out in a solvent such as benzene, toluene or dimethylformamide at temperatures between 80° and 150° C., preferably at 125° C. Conveniently, either the hydrazoic acid is liberated during the reaction from an alkali metal azide, e.g. sodium azide, in the presence of a weak acid such as ammonium chloride or a tetrazolide salt obtained in the reaction mixture during the reaction with a salt of hydrazoic acid, preferably with aluminium azide or tributyl tin azide, which is also preferably produced in the reaction mixture by reacting aluminium chloride or tributyl tin chloride with an alkali metal azide such as sodium azide, is subsequently liberated by acidification with a dilute acid such as 2N hydrochloric or 2N sulphuric acid.

If according to the invention a compound of general formula I is obtained wherein X is a group of the formula =N—CN, this may be converted by saponification into a corresponding compound of formula I wherein X denotes a group of the formula =N—CONH$_2$, or if a compound of formula I is obtained wherein $R_7$ denotes a carboxy group, this may be converted by esterification or amidation into a corresponding compound of formula I wherein $R_7$ denotes a group which can be metabolically converted into a carboxy group in vivo, an aminocarbonyl, alkylaminocarbonyl or dialkylaminocarbonyl group, or if a compound of formula I is obtained wherein $R_7$ denotes an aminocarbonyl group, this may be converted by dehydration into a corresponding compound of formula I wherein $R_7$ denotes a cyano group.

The subsequent saponification of a group of the formula =N—CN is carried out by acid- or base-catalysed hydrolysis, for example under the action of sulphuric or phosphoric acid, formic acid, hydrochloric acid, hydrobromic acid, acetic acid, boron trifluoride, titanium tetrachloride or a combination of H$_2$O$_2$ with sodium or potassium hydroxide solution, at temperatures between 0° and 100° C., preferably at 20° to 50° C.

The subsequent esterification or amidation is conveniently carried out in a solvent, e.g. in an excess of the alcohol used, such as methanol, ethanol or isopropanol, or of the amine used, such as ammonia, methylamine, n-propylamine or dimethylamine, in the presence of an acid activating agent such as thionyl chloride or hydrogen chloride gas, carbonyldiimidazole or N,N'-dicyclohexylcarbodiimide at temperatures of between −20° and 180° C., but preferably at ambient temperature.

The conversion of a carboxyl group into a group which is metabolically converted into a carboxy group in vivo is usefully performed by esterification with a corresponding alcohol or with a corresponding reactive acyl derivative, suitably in a solvent or solvent mixture such as water, methylene chloride, chloroform, ether, tetrahydrofuran, dioxane or dimethylformamide or in an excess of the acylating agent as solvent, optionally in the presence of an acid activating or dehydrating agent such as thionyl chloride, with the anhydrides, esters or halides thereof, optionally in the presence of an inorganic or tertiary organic base such as sodium hydroxide, potassium carbonate, triethylamine or pyridine, whilst these last two may simultaneously also be used as solvents, at temperatures between −25° and 100° C., but preferably at temperatures between −10° and 80° C. The subsequent dehydration is carried out with a dehydrating agent such as phosphorus pentoxide, sulphuric acid or p-toluenesulphonic acid chloride, optionally in a solvent such as methylene chloride or pyridine at temperatures between 0° and 100° C., preferably at temperatures between 20° and 80° C.

The compounds of formula I obtained may also be resolved into their enantiomers. Thus, the compounds of formula I obtained which contain only one optically active centre may be resolved into their optical antipodes using methods known per se (see Allinger N. L. and Eliel W. L. in "Topics in Stereochemistry", Vol. 6, Wiley Interscience, 1971), e.g. by recrystallisation from an optically active solvent or by reaction with an optically active substance, in particular a base, which forms salts with the racemic compound, and separating the salt mixture thus obtained, e.g. on the basis of their different solubilities, into the diastereomeric salts from which the free antipodes can be liberated by the action of suitable agents. The D- and L-forms of α-phenyl-ethylamine or cinchonidine are examples of particularly useful optically active bases.

Furthermore, the compounds of formula I obtained having at least 2 asymmetric carbon atoms can be resolved into their diastereomers on the basis of their physical-chemical differences using methods known per se, e.g. by chromatography and/or fractional crystallisation. A pair of enantiomers thus obtained can subsequently be resolved into the optical antipodes thereof, as described above. If, for example, a compound of formula I contains two optically active carbon atoms, the corresponding (R R', S S')- and (R S', S R')-forms are obtained.

In addition, the compounds of formula I thus obtained wherein $R_4$ and $R_5$ together represent a carbon-carbon bond, may be converted into their cis- and trans-isomers by conventional methods, e.g. by chromatography on a carrier such as silica gel or by crystallisation.

Furthermore, the new compounds of formula I thus obtained, should they contain a carboxy group, may, if desired, be converted subsequently into the addition salts thereof with inorganic or organic bases, or, if they contain a basic group, may, if desired, be converted subsequently into the salts thereof with inorganic or organic acids, more particularly, for pharmaceutical use, they may be converted into the physiologically acceptable addition salts thereof. Examples of bases include sodium hydroxide, potassium hydroxide, cyclohexylamine, ethanolamine, diethanolamine, triethanolamine, N-methylglucosamine, arginine and lysine and examples of acids include hydrochloric acid, hydrobromic acid, sulphuric acid, phosphoric acid, fumaric acid, succinic acid, lactic acid, citric acid, tartaric acid or maleic acid.

The compounds of formulae II to VIII used as starting materials may be obtained by methods known from the literature or are themselves known from the literature.

A compound of formula II used as starting material is obtained from a corresponding N-acylamino compound by Friedel-Craft acylation, subsequent deacylation, optionally followed by reduction, hydrolysis and/or esterification or is obtained by reacting a corresponding magnesium or lithium compound with a suitably substituted pyridine compound such as 3-cyano-pyridine, pyridine-3-aldehyde or a pyridine-3-carboxylic acid derivative, optionally followed by oxidation.

A compound of formula II used as starting material wherein $R_4$ and $R_5$ together denote a carbon-carbon bond is obtained by reacting a compound of general formula

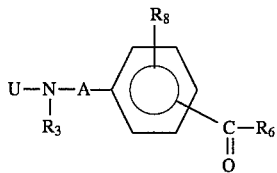

wherein $R_3$, $R_6$, $R_8$ and A are as hereinbefore defined and

U denotes a protective group for an amino group) with a compound of general formula

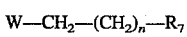

(wherein $R_7$ and n are as hereinbefore defined and

W denotes a triphenylphosphonium halide, dialkylphosphonic acid or magnesium halide group), with subsequent cleaving of the protective group used and optionally subsequent dehydration.

The reaction is preferably carried out in a suitable solvent such as diethylether, tetrahydrofuran, dioxane or dimethylformamide at temperatures between −30° and 100° C., preferably at temperatures between −20° and 25° C., optionally in the presence of a base.

The reaction with a triphenylphosphonium halide of formula X is, however, carried out to particular advantage in the presence of a base such as potassium tert.butoxide or sodium hydride.

If, in the reaction with a magnesium halide of formula X, the hydroxy group is not cleaved during the reaction from the carbinol which is primarily formed in the reaction mixture, this hydroxy group is cleaved in the presence of an acid such as hydrochloric acid, sulphuric acid, phosphoric acid or trichloroacetic acid or in the presence of a base such as sodium hydroxide or potassium hydroxide in a suitable solvent such as ethanol, isopropanol or dioxane at temperatures between 0° and 120° C., e.g. at temperatures between ambient temperature and the boiling temperature of the reaction mixture.

The subsequent dehydration is carried out with a dehydrating agent such as phosphorus pentoxide, sulphuric acid or p-toluenesulphonic acid chloride, optionally in a solvent such as methylene chloride or pyridine at temperatures between 0° and 100° C., preferably at temperatures between 20° and 80° C.

The compounds of formula III used as starting materials are obtained according to J. Heteroc. Chem. 19, 1205 (1982) either by reacting diphenoxydichloromethane with a correspondingly substituted amine or by reaction of carbon disulphide with a correspondingly substituted C-H acidic methyl or methylene component with subsequent methylation (Chem. Ber. 95, 2861 (1962)).

The compounds of formulae VI, VII and VIII used as starting materials are obtained by reacting a corresponding amino compound with a corresponding carbonic acid derivative.

The compounds of formula IX used as starting materials are obtained by Friedel-Craft's acylation of a corresponding amine.

The compounds of formula X used as starting materials are obtained by reacting a corresponding halogen compound with triphenylphosphane or with a trialkyl-phosphoester.

As already mentioned hereinbefore, the new compounds of general formula I wherein Y denotes an $R_1NR_2$— group and the physiologically acceptable salts thereof with inorganic or organic bases or acids have valuable pharmacological properties, particularly antithrombotic effects and an inhibitory effect on platelet aggregation. They are also thromboxane antagonists and thromboxane synthesis inhibitors, and it is particularly notable that the compounds of formula I have these effects simultaneously. They also have an effect on $PGE_2$ production in the lungs and on $PGD_2$, $PGE_2$ and $PGF_{2\alpha}$ production in human thrombocytes.

By way of example, the new compounds:

A=5E-6-(3-(2-cyano-3-cyclopropyl-guanidino)phenyl)-6-(3-pyridyl)hex-5-enoic acid, B=5E-6-(3-(2-cyano-3-tert.butyl-guanidino)phenyl)-6-(3-pyridyl)hex-5-enoic acid, C=5E-6-(3-(2-cyano-3-cyclopentyl-guanidino)phenyl)-6-(3-pyridyl)hex-5-enoic acid, D=5E-6-(3-(2-cyano-3-isopropyl-guanidino)phenyl)-6-(3-pyridyl)hex-5-enoic acid, E=5E-6-(3-(2-cyano-3-(exo-norborn-2-yl)guanidino)phenyl)-6-(3-pyridyl)hex-5-enoic acid, F=5E-6-(3-(2-cyano-3-(2-methylpropyl)guanidino)phenyl)-6-(3-pyridyl)hex-5-enoic acid, G=5E-6-(3-(2-cyano-3-neopentyl-guanidino)phenyl)-6-(3-pyridyl)hex-5-enoic acid, H=5E-6-(3-(2-cyano-3-pentyl-guanidino)phenyl)-6-(3-pyridyl)hex-5-enoic acid, I=5E-6-(3-(2-cyano-3-(3-methylbutyl)guanidino)phenyl)-6-(3-pyridyl)hex-5-enoic acid, J=5E-6-(3-(2,2-dicyano-1-(2-methylpropylamino)ethyleneamino)phenyl)-6-(3-pyridyl)hex-5-enoic acid, K=5E-6-(3-(2,2-dicyano-1-isopropylaminoethyleneamino)phenyl)-6-(3-pyridyl)hex-5-enoic acid, L=5E-6-(3-(2,2-dicyano-1-(3-methylbutylamino)ethyleneamino)phenyl)-6-(3-pyridyl)hex-5-enoic acid, M=5E-6-(3-(2,2-dicyano-1-cyclopentylaminoethyleneamino)-phenyl)-6-(3-pyridyl)hex-5-enoic acid, N=5E-6-(3-(2,2-dicyano-1-neopentylaminoethyleneamino)phenyl)-6-(3-pyridyl)hex-5-enoic acid, O=5E-6-(3-(2,2-dicyano-1-cyclopropylaminoethyleneamino)phenyl)-6-(3-pyridyl)hex-5-enoic acid, P=5E-6-(3-(2,2-dicyano-1-propylamino-ethyleneamino)phenyl)-6-(3-pyridyl)hex-5-enoic acid, Q=5E-6-(3-(2,2-dicyano-1-tert.butylaminoethyleneamino)phenyl)-6-(3-pyridyl)hex-5-enoic acid, R=5E-6-(4-(2-cyano-3-cyclohexyl-guanidino)phenyl)-6-(3-pyridyl)hex-5-enoic acid, S=6-(3-(2-cyano-3-tert.butyl-guanidino)phenyl)-6-(3-pyridyl)hexanoic acid, T=5E-6-(3-(1-neopentylamino-2-nitro-ethyleneamino)phenyl)-6-(3-pyridyl)hex-5-enoic acid, U=E/Z-6-(4-(2-(2-cyano-3-tert.butyl-guanidino)ethyl)phenyl)-6-(3-pyridyl)hex-5-enoic acid, V=5E-6-(3-(3-tert.butyl-2-phenylsulphonyl-guanidino)phenyl)-6-(3-pyridyl)hex-5-enoic acid, W=5E-6-(3-(2-amidosulphonyl-3-(2-methylpropyl)guanidino)phenyl)-6-(3-pyridyl)hex-5-enoic acid, X=5E-6-(3-(2-carbamoyl-2-cyano-1-(2-methylpropylamino)-ethyleneamino)phenyl)-6-(3-pyridyl)hex-5-enoic acid and Y=4E-1-(5-(3-(2-cyano-3-cyclopentyl-guanidino)phenyl)-5-(3-pyridyl)-pent-4-enyl)tetrazole were tested for their biological properties as follows:

Antithrombotic Activity

Procedure

The thrombocyte aggregation is measured using the method of Born and Cross (J. Physiol. 170, 397 (1964)) in platelet-rich plasma taken from healthy volunteers. To inhibit coagulation, the blood is mixed with 3.14% strength sodium citrate in a ratio by volume of 1:10.

Collagen-induced Aggregation

The pattern of decrease in the optical density of the platelet suspension is photometrically measured and recorded after the addition of the aggregation-triggering substance. The rate of aggregation is concluded from the angle of inclination of the density curve. The point on the curve where there is greatest light transmittance is used to calculate the "optical density".

The quantity of collagen used is as little as possible but sufficient to produce an irreversible reaction curve. Standard commercial collagen produced by Hormonchemie of Munich is used. Before the addition of the collagen the plasma is incubated for 10 minutes with the substance at 37° C.

From the measurements obtained an $EC_{50}$ is determined by plotting a graph, and indicates a 50% change in the "optical density" in terms of the inhibition of aggregation.

Thromboxane-antagonistic Activity

Venous human blood is anti-coagulated with 13 mM $Na_3$ citrate and centrifuged for 10 minutes at 170×g. The supernatant platelet-rich plasma is passed through a Sepharose 2B column in order to remove the plasma proteins. Aliquots of the platelet suspension obtained are incubated with the test substance, the ligand ($^3$H-labelled) and a marker ($^{14}$C-labelled) for 60 minutes at ambient temperature and then centrifuged for 20 seconds at 10,000×g. The supernatant is removed and the pellet is dissolved in NaOH. The $^3$H activity in the supernatant corresponds to the free ligand, $^{14}$C gives the concentration of the marker. $^3$H in the pellet corresponds to the bound ligand whilst $^{14}$C is used to correct for the ligand in the extracellular space. After the process has been repeated, the displacement curve is determined from the binding values for different concentrations of the test substance and the $IC_{50}$ is determined.

Determining the Inhibitory Effect on Thromboxane Synthetase

Venous human blood is anti-coagulated with 13 mM $Na_3$ citrate and centrifuged for 10 minutes at 170×g. The supernatant platelet-rich plasma is passed through a Sepharose 2B column in order to remove the plasma proteins. Aliquots of the platelet suspension obtained are incubated with the test substance or with a solvent as control for 10 minutes at ambient temperature and after the addition of $^{14}$C-labelled arachidonic acid incubation is continued for a further 10 minutes. After this has been stopped with 50 µl of citric acid, extraction is carried out 3 times with 500 µl of ethyl acetate and the combined extracts are distilled off with nitrogen. The residue is taken up in ethyl acetate, placed on TLC film and separated with chloro-form:methanol:glacial acetic acid:water (90:8:1:0.8, v/v/v/v). The dried TLC films are placed on X-ray film for 3 days, the autoradiograms were developed and the active zones were marked on the film using the autoradiograms. After cutting out, the activity is measured in a scintillation counter and the inhibition of the formation of TXB2 is calculated. The $IC_{50}$ is determined by linear interpolation.

The following Table shows the values found:

| Example | Inhibition of thromboxane synthetase $IC_{50}$ | Thromboxane-antagonistic activity $IC_{50}$ | Inhibition of collagen-induced aggregation $EC_{50}$ |
|---|---|---|---|
| A | 0.380 µM/l | 0.017 µM/l | 0.90 µM/l |
| B | 0.004 µM/l | 0.011 µM/l | 0.50 µM/l |
| C | 0.003 µM/l | 0.030 µM/l | 0.53 µM/l |
| D | 0.024 µM/l | 0.018 µM/l | 0.40 µM/l |
| E | 0.004 µM/l | 0.017 µM/l | 0.75 µM/l |
| F | 0.030 µM/l | 0.007 µM/l | 0.35 µM/l |
| G | 0.014 µM/l | 0.022 µM/l | 0.26 µM/l |
| H | 0.005 µM/l | 0.025 µM/l | 0.64 µM/l |
| I | 0.003 µM/l | 0.027 µM/l | 0.69 µM/l |
| J | 0.030 µM/l | 0.002 µM/l | 0.12 µM/l |
| K | 0.045 µM/l | 0.002 µM/l | 0.02 µM/l |
| L | 0.031 µM/l | 0.015 µM/l | 1.20 µM/l |
| M | 0.033 µM/l | 0.001 µM/l | 0.05 µM/l |
| N | 0.044 µM/l | 0.003 µM/l | 0.62 µM/l |
| O | 0.065 µM/l | 0.062 µM/l | 0.04 µM/l |
| P | 0.040 µM/l | 0.037 µM/l | 0.05 µM/l |
| Q | 0.050 µM/l | 0.050 µM/l | 0.12 µM/l |
| R | 0.180 µM/l | 1.300 µM/l | 31.00 µM/l |
| S | 0.037 µM/l | 0.120 µM/l | 1.10 µM/l |
| T | 0.290 µM/l | 0.280 µM/l | 9.50 µM/l |
| U | 0.007 µM/l | 0.050 µM/l | 1.20 µM/l |
| V | 0.004 µM/l | 0.055 µM/l | 3.00 µM/l |
| W | 2.700 µM/l | 0.600 µM/l | 12.00 µM/l |
| X | 0.005 µM/l | 0.380 µM/l | 31.00 µM/l |
| Y | 0.250 µM/l | 0.021 µM/l | 1.20 µM/l |

Acute Toxicity

The acute toxicity of the substances being tested was determined as a guide on groups of 10 mice after oral administration of a single dose of 250 mg/kg (observation period: 14 days). At this dose, none of the animals died.

In view of their pharmacological properties, the new compounds and the physiologically acceptable addition salts thereof are suitable for the treatment and prevention of thromboembolic disorders such as coronary infarct, cerebral infarct, so-called transient ischaemic attacks, Amaurosis fugax and for the prevention of arteriosclerosis and metastasis and for treating ischaemia, asthma and allergies.

The new compounds and the physiologically acceptable addition salts thereof are also suitable in the treatment of diseases involving thromboxane-mediated constriction or $PGE_2$-mediated dilation of the capillaries, e.g. in pulmonary hypertension. Moreover, these may be used to reduce the severity of a transplant rejection, in order to decrease the renal toxicity of substances such as cyclosporin, in order to treat kidney diseases, more particularly for the therapy or prevention of kidney changes connected with hypertension, systemic lupus or ureter blockages and in cases of shock in conjunction with sepsis, trauma or burns.

The dose required to achieve such an effect is expediently 0.3 to 4 mg/kg of body weight, preferably 0.3 to 2 mg/kg of body weight, two to four times a day. For this purpose, the compounds of formula I according to the invention, optionally combined with other active substances, may be made into conventional galenic preparations such as tablets, coated tablets, capsules, powders, suspensions or suppositories, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetyl stearyl alcohol, carboxymethylcellulose or fatty substances such as hard fat or suitable mixtures thereof.

The present invention further relates to new pharmaceutical compositions containing a compound of formula I prepared according to the invention and a PDE- inhibitor or a lysing agent.

Examples of PDE-inhibitors include:
2,6-bis(diethanolamino)-4,8-dipiperidino-pyrimido[5,4-d]pyrimidine (Dipyridamole),
2,6-bis(diethanolamino)-4-piperidino-pyrimido [5,4-d]pyrimidine (Mopidamole),
2-(4-methoxy-phenyl)-5(6)-(5-methyl-3-oxo-4,5-dihydro-2H-6-pyridazinyl)-benzimidazole (Pimobendan),
2-(4-hydroxy-phenyl)-5(6)-(5-methyl-3-oxo-4,5-dihydro-2H-6 -pyridazinyl)-benzimidazole,
1-(1-oxido-thiomorpholino)-3-piperazino-5-methyl-iso-quinoline,
6-[4-(3,4-dichlorophenylsulphinyl)-butoxy]-3,4-dihydro-carbostyrile and
6-[4-(2-pyridylsulphonyl)-butoxy]carbostyrile,
whilst the oral daily dose is
for dipyridamole 2.5 to 7.5 mg/kg, preferably 5 mg/kg,
for mopidamole 15 to 25 mg/kg, preferably 20 mg/kg,
for 2-(4-methoxy-phenyl)-5(6)-(5-methyl-3-oxo-4,5-dihydro-2H-6-pyridazinyl)-benzimidazole 0.05 to 0.15 mg/kg, preferably 0.08 to 0.10 mg/kg,
for 2-(4-hydroxy-phenyl)-5(6)-(5-methyl-3-oxo-4,5-dihydro-2H-6-pyridazinyl)-benzimidazole 0.05 to 0.15 mg/kg, preferably 0.08 to 0.10 mg/kg,
for 1-(1-oxido-thiomorpholino)-3-piperazino-5-methylisoquinoline 0.20 to 2.00 mg/kg, preferably 0.40 to 1.00 mg/kg,
for 6-[4-(3,4-dichlorophenylsulphinyl)-butoxy]-3,4-dihydrocarbostyrile 0.10 to 1.00 mg/kg, preferably 0.20 to 0.50 mg/kg and
for 6-[4-(2-pyridylsulphonyl)-butoxy]carbostyrile 0.10 to 1.00 mg/kg, preferably 0.20 to 0.50 mg/kg.

Suitable lysing agents are plasminogen activators such as t-PA, rt-PA, streptokinase, eminase or urokinase, whilst the lysing agents may be administered parenterally but are preferably given by intravenous route, e.g. t-PA or rt-PA is given in a dosage of between 15 and 100 mg per patient, urokinase is given in a dose between 250,000 and 3,000,000 units per patient, eminase is given in a dose of about 30 mg per patient and streptokinase is given in a dose of between $5 \times 10^4$ and $3 \times 10^7$ IU within 5 minutes and 24 hours, respectively.

For pharmaceutical use, a new combination containing 1 to 500 mg of a PDE-inhibitor, preferably 2 to 75 mg, and 10 to 300 mg, preferably 10 to 200 mg, of a compound of formula I prepared according to the invention or a physiologically acceptable addition salts thereof, incorporated together with one or more inert conventional carriers and/or diluents, e.g. corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, can be used to produce conventional galenic preparations such as plain or coated tablets, capsules, powders, suspensions or suppositories. These are administered to adults 2 to 4 times a day, preferably 3 to 4 times a day, in order to achieve the desired effect.

Moreover, for pharmaceutical use, a new combination can be used containing a lysing agent in the dosages mentioned above together with 10 to 300 mg, preferably 10 to 200 mg, of a compound of formula I prepared according to the invention or a physiologically acceptable addition salt thereof, incorporated into conventional parenteral preparations, preferably conventional intravenous preparations such as ampoules or infusions, which dosage may be administered within 5 minutes and 24 hours.

Obviously, the active substances of the above-mentioned combinations may also be administered individually, if desired.

The Examples which follow illustrate the invention:

Preparation of the Starting Materials

Example I

Methyl 6-(4-aminophenyl)-6-(3-pyridyl)hex-5-enoate
a) 4-acetylaminophenyl-3-pyridyl-ketone
980 g of aluminium trichloride are slowly mixed with 155 ml of dimethylformamide. To this mixture are added successively at 90° to 110° C. 342 g of nicotinic acid chloride hydrochloride and 206 g of N-acetylaniline. The reaction mixture is then mixed with 600 ml of ethylene chloride, poured onto ice and neutralised by the addition of 15N sodium hydroxide solution whilst cooling. The aqueous phase is extracted with methylene chloride. The combined organic phases are evaporated down and the residue is recrystallised from methanol.

Yield: 44% of theory, Melting point: 189°–191° C. $C_{14}H_{12}N_2O_3$ (240.26) Calculated: C 69.99 H 5.03 N 11.66 Found: 69.87 5.14 11.58 b) 6-(4-acetylaminophenyl)-6-(3-pyridyl)hex-5-enoic acid
To a suspension of 307 g of 4-carboxybutyltriphenylphosphonium bromide and 233 g of potassium tert.butoxide in 2.8 liters of tetrahydrofuran are added, at –40° C., 140 g of 4-acetylaminophenyl-3-pyridyl-ketone and this mixture is stirred for 2 hours. The reaction mixture is decomposed by the addition of ice water and evaporated down. The residue is taken up in water and washed with ethyl acetate. The aqueous phase is acidified to pH 5 to 6 and extracted with ethyl acetate. The organic phase is concentrated by evaporation and the residue is recrystallised from ethyl acetate/diisopropylether.

Yield: 86% of theory, Melting point: 155°–156° C. $C_{19}H_{20}N_2O_3$ (324.38) Calculated: C 70.35 H 6.21 N 8.64 Found: 70.19 6.27 8.66 c) Methyl 6-(4-aminophenyl)-6-(3-pyridyl)hex-5-enoate
65 g of 6-(4-acetylaminophenyl)-6-(3-pyridyl)hex-5-enoic acid are refluxed for 2 hours in a mixture of 300 ml of methanol and 150 ml of saturated methanolic hydrochloric acid. The reaction mixture is combined with 500 ml of water, neutralised by adding sodium carbonate and extracted with ethyl acetate. The organic phase is washed, dried and evaporated down.

Yield: 71% of theory, Oil, $R_f$ value: 0.72 (silica gel; dichloromethane/acetone=9:1) $C_{18}H_{20}N_2O_2$ (296.37) Calculated: C 72.95 H 6.80 N 9.45 Found: 72.83 6.85 9.23

The following compound is obtained analogously to Example I:
Methyl 6-(4-methylaminophenyl)-6-(3-pyridyl)hex-5-enoate Oil, $R_f$ value: 0.56 (silica gel; dichloromethane/ethanol=20:1) $C_{19}H_{22}N_2O_2$ (310.40) Calculated: C 73.52 H 7.14 N 9.03 Found: 73.35 7.24 8.91

Example II

Methyl 6-(3 -aminophenyl)-6-(3 -pyridyl)hex-5-enoate
a) 3-Acetylaminophenyl-3-pyridyl ketone
114 g of 3-nitrophenyl-3-pyridyl ketone are hydrogenated in 1000 ml of acetic acid and 35 g of Raney nickel for 2 hours at 50° C. under 5 bar. The catalyst is filtered off and the filtrate is combined with 80 ml of acetic anhydride. After 30 minutes at ambient temperature the mixture is evaporated down and the residue is taken up in ethyl acetate. The organic phase is washed with aqueous potassium carbonate solution and dried over sodium sulphate. The solvent is removed and the residue is recrystallised from ethyl acetate/diisopropylether.

Yield: 69% of theory, Melting point: 116°–117° C. $C_{14}H_{12}N_2O_2$ (240.26) Calculated: C 69.99 H 5.03 N 11.66 Found: 70.01 5.11 11.81 b) 6-(3-Acetylaminophenyl)-6-(3-pyridyl)hex-5-enoic acid

To a mixture of 217 g of 4-carboxybutyl-triphenylphosphonium bromide and 154 g of potassium tert.butoxide in 1.8 liters of tetrahydrofuran are added, at −25° C., 94 g of 3-acetylaminophenyl-3-pyridyl ketone. After 2 hours stirring at ambient temperature the reaction mixture is combined with 200 ml of water and then substantially evaporated down. The residue is taken up in 500 ml of water and washed with ethyl acetate. The aqueous phase is then neutralised by the addition of citric acid and extracted with ethyl acetate. The organic phase is evaporated down and the residue is recrystallised from ethyl acetate/acetone.

Yield: 85% of theory, Melting point: 86°–89° C. $C_{19}H_{20}N_2O_3$ (324.38) Calculated: C 70.35 H 6.21 N 8.64 Found: 70.15 6.36 8.50 c) Methyl 6-(3-aminophenyl)-6-(3-pyridyl)hex-5-enoate 65 g of 6-(3-acetylaminophenyl)-6-(3-pyridyl)hex-5-enoic acid are refluxed for 4 hours in a mixture of 400 ml of methanol and 200 ml of methanolic hydrochloric acid. The solvent is removed and the residue is taken up in water. The aqueous phase is washed with ethyl acetate and adjusted to pH 8–9 by the addition of 4N sodium hydroxide solution. The aqueous phase is extracted with ethyl acetate. The organic phase is washed, dried and evaporated down.

Yield: 71% of theory, Oil, $R_f$ value: 0.55 (silica gel; dichloromethane/ethanol=9:1) $C_{18}H_{20}N_2O_2$ (296.37) Calculated: C 72.95 H 6.80 N 9.45 Found: 72.83 6.91 9.18

The following compounds are obtained analogously to Example II

Methyl 5-(3-aminophenyl)-5-(3-pyridyl)pent-4-enoate Resin, $R_f$ value: 0.58 (silica gel; dichloro-methane/ethanol= 20:1) $C_{17}H_{18}N_2O_2$ (282.34) Calculated: C 72.32 H 6.43 N 9.92 Found: 72.29 6.55 9.70

Methyl 7-(3-aminophenyl)-7-(3-pyridyl)hept-6-enoate Resin, $R_f$ value: 0.63 (silica gel; dichloro-methane/ethanol= 20:1) $C_{19}H_{22}N_2O_2$ (310.40) Calculated: C 73.52 H 7.14 N 9.03 Found: 73.41 7.18 8.89

Methyl 8-(3-aminophenyl)-8-(3-pyridyl)oct-7-enoate Oil, $R_f$ value: 0.66 ( silica gel; dichloro-methane/ethanol=20:1) $C_{20}H_{24}N_2O_2$ (324.44) Calculated: C 74.05 H 7.46 N 8.63 Found: 73.92 7.49 8.48

Example III

Methyl 6-(3-methylaminophenyl)-6-(3-pyridyl)hex-5-enoate a) N-acetyl-3-methylaminophenyl-3-pyridylketone To 84 g of 3-acetylaminophenyl-3-pyridylketone in 600 ml of dimethylformamide are added in batches with cooling 17 g of sodium hydride followed by 22 ml of methyliodide. The mixture is stirred for one hour at ambient temperature and the reaction mixture is decomposed by the addition of 100 ml of water. The solvent is drawn off and the residue is taken up in ethyl acetate. The organic phase is washed, dried and evaporated down. The residue is purified over a silica gel column with dichloromethane/ethanol (30:1).

Oil, $R_f$ value: 0.45 (silica gel; dichloro-methane/ethanol= 30:1) $C_{15}H_{14}N_2O_2$ (254.29) Calculated: C 70.85 H 5.55 N 11.02 Found: 70.96 5.65 10.92 b) Methyl 6-(3-methyl aminophenyl)-6-(3-pyridyl)hex-5-enoate

Prepared from N-acetyl-3-methylaminophenyl-3-pyridylketone and 4-carboxybutyl-triphenylphosphonium bromide analogously to Example IIb and subsequent esterification analogously to Example IIc.

Oil, $R_f$ value: 0.56 (silica gel; dichloromethane/ethanol= 20:1) $C_{19}H_{22}N_2O_2$ (310.40) Calculated: C 73.52 H 7.14 N 9.03 Found: 73.53 7.20 8.84

Example IV

Methyl 6-(3-amino-4-methylphenyl)-6-(3-pyridyl)hex-5-enoate a) 4-Methyl-3-nitrophenyl-3-pyridylketone Into a mixture of 22 ml of conc. sulphuric acid and 16 ml of fuming nitric acid cooled to 5° to 10° C. are added, in batches, 16.4 g of 4-methylphenyl-3-pyridylketone. The reaction mixture is then stirred for 2 hours at ambient temperature, poured onto ice and made alkaline by the addition of conc. ammonia. The aqueous phase is extracted with ethyl acetate. The organic phase is dried, concentrated by evaporation and the residue is purified over a silica gel column with ethyl acetate/cyclohexane=1:1. The product fraction is evaporated down and the residue is recrystallised from ethyl acetate/diisopropylether.

Yield: 60% of theory, $C_{13}H_{10}N_2O_3$ (242.24) Calculated: C 64.46 H 4.16 N 11.56 Found: 64.42 4.19 11.64 b) 3-Acetylamino-4-methylphenyl-3-pyridylketone 12 g of 4-methyl-3-nitrophenyl-3-pyridylketone are dissolved in a mixture of 120 ml of ethyl acetate and 15 ml of methanol and after the addition of 2 g of Raney nickel the mixture is hydrogenated for 3 hours at 50° C. under a hydrogen pressure of 3.5 bar. The catalyst is filtered off, the filtrate is evaporated down and the residue is taken up in 30 ml of glacial acetic acid. The solution is mixed with 10 ml of acetic anhydride and stirred for 1 hour at ambient temperature. The reaction mixture is evaporated down, the residue is taken up in ethyl acetate and washed with 2N sodium carbonate solution. The organic extract is dried, evaporated down and the residue is recrystallised from ethyl acetate/diisopropylether.

Yield: 77% of theory, Melting point: 92°–94° C. $C_{15}H_{14}N_2O_2$ (254.29) Calculated: C 70.85 H 5.55 N 11.02 Found: 70.77 5.64 10.96

The following compound is obtained analogously to Example IVb:

3-Acetylamino-5-trifluoromethylphenyl-3-pyridylketone. Melting point: 128° C. (ethyl acetate/diisopropylether) $C_{15}H_{11}F_3N_2O_2$ (308.26) Calculated: C 58.45 H 3.59 N 9.09 58.42 3.72 9.10 c) 6-(3-Acetylamino-4-methylphenyl)-6-(3-pyridyl)hex-5enoic acid

Preparation as in Example Ib.

Yield: 70% of theory, Melting point: 177°–179° C. (isopropanol/diisopropylether) $C_{20}H_{22}N_2O_3$ (338,41) Calculated: C 70.99 H 6.55 N 8.28 Found: 70.83 .6.46 8.19

The following compound is obtained analogously to Example IVc 6-(3-Acetylamino-5-trifluoromethylphenyl)-6-(3-pyridyl)-hex- 5-enoic acid Melting point: 164° C. (dichloromethane) $C_{20}H_{19}F_3N_2O_3$ (392.38) Calculated: C 61.22 H 4.88 N 7.14 Found: 61.17 4.79 7.05 d) Methyl 6-(3-amino-4-methylphenyl)-6-(3-pyridyl)hex-5-enoate

Preparation as in Example Ic.

Yield: 92% of theory, Oil, $R_f$ value: 0.34 (silica gel; dichloromethane/acetone=9:1) $C_{19}H_{22}N_2O_2$ (310.40) Calculated: C 73.52 H 7.14 N 9.03 Found: 73.35 7.28 8.86

The following compound is obtained analogously to Example IV:

Methyl 6-(3-amino-5-trifluoromethylphenyl)-6-(3-pyridyl)hex-5-enoic acid Oil, $R_f$ value: 0.46 (silica gel; dichloromethane/ethanol=10:1) $C_{19}H_{19}F_3N_2O_2$ (364.37) Calculated: C 62.63 H 5.26 N 7.69 Found: 62.55 5.24 7.72

Example V

3-Nitro-5-trifluoromethylphenyl-3-pyridylketone

To 101 g of 5-trifluoromethylphenyl-3-pyridylketone are added carefully, one after the other, 400 ml of conc. sulphuric acid, 200 ml of oleum and 140 ml of fuming nitric acid, whilst the internal temperature should not exceed 35° C. The reaction mixture is stirred for 12 hours at ambient temperature and then poured onto 3 kg of ice. The reaction solution is neutralised by the addition of 50% sodium hydroxide solution, during which the nitrate salt is precipitated. This is suction filtered and then dissolved in 6N sodium hydroxide solution. The aqueous phase is extracted with ethyl acetate. The organic extract is dried and evaporated down, the oil obtained crystallises when left to stand.

Yield: 68% of theory, Melting point: 182°–184° C. $C_{13}H_7F_3N_2O_3$ (296.20) Calculated: C 52.71 H 2.38 N 9.46 Found: 52.56 2.45 9.55

Example VI 4E-1-(5-(3-Aminophenyl)-5-(3-pyridyl)pent-4-enyl)tetrazole a) 4E-5-(3-Acetylaminophenyl)-5-(3-pyridyl)pent-4-enecarbonitrile To a suspension of 25.5 g of 4-cyanobutyl-triphenylphosphonium bromide and 14 g of potassium tert.butoxide in 200 ml of tetrahydrofuran are added, at −40° C., 12 g of 3-acetylaminophenyl-3-pyridylketone. The mixture is stirred for 3 hours at ambient temperature and the reaction mixture is decomposed by the addition of 50 ml of ice water. The mixture is concentrated by evaporation, the residue is taken up in water and extracted with ethyl acetate. The organic phase is evaporated down and the residue is purified over a silica gel column with dichloromethane/ethanol=40:1. The product fraction is evaporated down and the residue is recrystallised from ethyl acetate/diisopropylether.

Yield: 71% of theory, Melting point: 144°–146° C. $C_{19}H_{19}N_3O$ (305.38) Calculated: C 74.73 H 6.27 N 13.76 Found: 74.57 6.14 13.59 b) 4E-1-(5-(3-Acetylaminophenyl)-5-(3-pyridyl)pent-4-enyl)-tetrazole 5.8 g of 4E-5-(3-acetylaminophenyl)-5-(3-pyridyl)pent-4-encarbonitrile and 9.96 g of tributyl tin azide are refluxed for 48 hours in 300 ml of toluene. The organic phase is extracted with 100 ml of 1N sodium hydroxide solution. The aqueous phase is washed with ethyl acetate and adjusted to a pH of 4–5 by the addition of citric acid. The precipitate formed is suction filtered, washed with water and dried.

Yield: 83% of theory, Melting point: 174°–175° C. $C_{19}H_{20}N_6O$ (348.41) Calculated: C 65.50 H 5.79 N 24.12 Found: 65.39 5.86 23.96 c) 4E-1-(5-(3-Aminophenyl)-5-(3-pyridyl)pent-4-enyl)tetrazole 5.7 g of 4E-1-(5-(3-acetylaminophenyl)-5-(3-pyridyl)-pent-4-enyl)tetrazole are heated in 60 ml of 4N hydrochloric acid for 5 hours at 60° C. The reaction solution is neutralised by the addition of sodium bicarbonate and then adjusted to a pH value of 4–5 by the addition of citric acid. The aqueous phase is extracted with dichloromethane/methanol=4:1. The organic phase is washed with saturated sodium chloride solution, dried and concentrated by evaporation.

Yield: 91% of theory, Oil, $R_f$ value: 0.49 (silica gel RP8; 5% sodium chloride solution/methanol=4:6) $C_{17}H_{18}N_6$ (306.37) Calculated: C 66.65 H 5.92 N 27.43 Found: 66.53 6.04 27.21

Example 1

5E-6-(4-(2-Cyano-3-cyclohexyl-guanidino)phenyl)-6-(3-pyridyl)hex-5-enoic acid a) Methyl 5E-6-(4-cyanimido-phenoxymethyleneamido)phenyl)-6-(3-pyridyl)hex-5-enoate 11.4 g of diphenoxymethylene-cyanamide (J. Heteroc. Chem. 19, 1205 (1982)) and 15 g of methyl 5E-6-(4-(aminophenyl)-6-(3-pyridyl)hex-5-enoate are dissolved in 250 ml of isopropanol and stirred for 6 hours at ambient temperature. The precipitate formed is suction filtered and washed with diethylether.

Yield: 87% of theory, Melting point: 163°–165° C. $C_{26}H_{24}N_4O_3$ (440.50) Calculated: C 70.89 H 5.49 N 12.77 Found: 70.67 5.51 12.50 b) 5E-6-(4-(2-Cyano-3-cyclohexyl-guanidino)phenyl)-6-(3-pyridyl)hex-5-enoic acid 2.2 g of methyl 5E-6-(4-(cyanimido-phenoxymethyleneamino)phenyl)-6-(3-pyridyl)hex-5-enoate and 0.8 g of cyclohexylamine are refluxed in 40 ml of isopropanol for 2 hours. The still hot reaction mixture is filtered, the filtrate is mixed at 40°–50° C. with 6 ml of 2N sodium hydroxide solution and stirred for 2 hours at 40°–50° C. The reaction solution is evaporated down and the residue is taken up in water. The aqueous phase is washed with ethyl acetate and adjusted to pH 4–5 by the addition of citric acid. The aqueous phase is extracted with ethyl acetate. The organic extract is washed with water, dried and evaporated down. The residue is recrystallised from ethyl acetate/isopropanol.

Yield: 40% of theory, Melting point: 145°–147° C. $C_{25}H_{29}N_5O_2$ (431.54) Calculated: C 69.58 H 6.77 N 16.23 Found: 69.53 7.01 15.98

The following compounds are obtained analogously to Example 1:

(1) 5E-6-(4-(2-Cyano-3-cyclopropyl-guanidino)phenyl)-6-(3-pyridyl)hex-5-enoic acid Melting point: 118° C. (ethyl acetate/isopropanol) $C_{22}H_{23}N_5O_2$ (389.46) Calculated: C 67.85 H 5.95 N 17.98 Found: 67.61 6.04 17.79

(2) E/Z-6-(4-(2-Cyano-3-cyclopropyl-1-methyl-guanidino)phenyl)-6-(3-pyridyl)hex-5-enoic acid Starting from methyl 6-(4-methylaminophenyl)-6-(3-pyridyl)hex-5-enoate; end product purified by column chromatography on silica gel with dichloro-methane/ethanol=20:1. Foam, $R_f$ value: 0.25 (silica gel; dichloromethane/ethanol=20:1). $C_{23}H_{25}N_5O_2$ (403.49) Calculated: C 68.47 H 6.25 N 17.36 Found: 68.24 6.40 17.52

Example 2

5E-6-(3-(2-Cyano-3-(2-hydroxy-1,1-dimethyl ethyl)-guanidino)phenyl)-6-(3-pyridyl)hex-5-enoic acid a) Methyl 5E-6-(3-(cyanimido-phenoxymethyleneamino)phenyl)- 6-(3-pyridyl)hex-5-enoate acid 8.4 g of diphenoxymethylene-cyanamide and 10.5 g of methyl 5E-6-(3-aminophenyl)-6-(3-pyridyl)hex-5-enoate are dissolved in 100 ml of isopropanol and stirred for 5 hours at ambient temperature. The reaction mixture is then evaporated down and the residue is purified over a silica gel column with dichloromethane/ethanol=40:1.

Yield: 86% of theory, Resin, $R_f$ value: 0.61 (silica gel; dichloromethane/ethanol=20:1). $C_{26}H_{24}N_4O_3$ (440.50) Calculated: C 70.89 H 5.49 N 12.72 Found: 70.68 5.60 12.79

The following compounds are obtained analogously to Example 2a (1) Methyl 5E-6-(3-(cyanimido-phenoxy-methyleneamino)-4-methylphenyl)-6-(3-pyridyl)hex-5-enoate Melting point: 147°–149° C. (ethyl acetate/diiso-propylether) $C_{27}H_{26}N_4O_3$ (454.53) Calculated: C 71.35 H 5.77 N 12.33 Found: 71.19 5.92 12.26

(2) Methyl 5E-6-(3-(cyanimido-phenoxy-methyleneamino)-5-trifluoromethylphenyl)-6-(3-pyridyl)hex-5-enoate Melting point: 148°–149° C. (diethylether) $C_{27}H_{23}F_3N_4O_3$ (508.5) Calculated: C 63.78 H 4.56 N 11.02 Found: 63.67 4.61 11.11 b) 5E-6-(3-(2-Cyano-3-(2-hydroxy-1,1-dimethylethyl)guanidino)phenyl)-6-(3-pyridyl)hex-5-enoic acid 2.2 g of methyl 5E-6-(3-(cyanimido-phenoxymethyleneamino)phenyl)-6-(3-pyridyl)hex-5-enoate and 2 ml of 2-hydroxy1,1-dimethylethylamine are refluxed for 6 hours in 22 ml of isopropanol. The still hot reaction mixture is filtered and mixed with 15 ml of 2N sodium hydroxide solution at 50° C. The reaction solution is stirred for one hour at 50° C., then concentrated by evaporation and the residue is taken up in water. The aqueous phase is washed with ethyl acetate and then adjusted to pH 4–5 by the addition of citric acid. The aqueous phase is extracted with ethyl acetate, the organic extract is dried and evaporated down. The residue is purified over a silica gel column with dichloromethane/ethanol= 19:1. The product fraction is evaporated down and the residue is recrystallised from ethyl acetate/diisopropylether.

Yield: 13% of theory, Melting point: 155° C. (decomp.) $C_{23}H_{27}N_5O_3$ (421.50) Calculated: C 65.54 H 6.46 N 16.62 Found: 65.57 6.36 16.41

The following compounds are obtained analogously to Example 2:

(1) 5E-6-(3-(2-Cyano-3-(2-phenylethyl)guanidino)phenyl)-6-(3-pyridyl)hex-5-enoic acid Melting point: 164° C. (decomp., water/isopropanol) $C_{27}H_{27}N_5O_2$ (453.50) Calculated: C 71.50 H 6.00 N 15.44 Found: 71.34 6.13 15.26

(2) 5E-6-(3-(2-Cyanimido-(4-phenylpiperazin-1-yl)methyleneamino)phenyl)- 6-(3-pyridyl)hex-5-enoic acid Melting point: 125° C. (decomp., water/isopropanol) $C_{29}H_{30}N_6O_2$ (494.61) Calculated: C 70.42 H 6.11 N 16.99 Found: 70.20 5.99 17.19

(3) 5E-6-(3-(Cyanimido-(4-phenylpiperidin-1-yl)methyleneamino)phenyl)- 6-(3-pyridyl)hex-5-enoic acid Melting point: 119° C. (decomp., water/isopropanol) $C_{30}H_{31}N_5O_2$ (493.60) Calculated: C 73.00 H 6.33 N 14.19 Found: 72.73 6.25 14.05

(4) 5E-6-(3-(Cyanimido-(1,2,3,4-tetrahydroisoquinolin-2-yl)methyleneamino)phenyl)-6-(3-pyridyl)hex-5-enoic acid Melting point: 194° C. (decomp., water/isopropanol) $C_{28}H_{27}N_5O_2$ (465.60) Calculated: C 72.24 H 5.85 N 15.04 Found: 72.06 5.97 14.94

(5) 5E-6-(3-(2-Cyano-3-(indan-2-yl)guanidino)phenyl)-6-(3-pyridyl)hex-5-enoic acid Melting point: 132° C. (decomp., ethyl acetate) $C_{28}H_{27}N_5O_2$ (465.60) Calculated: C 72.24 H 5.85 N 15.04 Found: 72.07 5.88 14.82

(6) 5E-6-(3-(2-Cyano-3-cyclopropyl-guanidino)phenyl)-6-(3-pyridyl)hex-5-enoic acid Melting point: 125° C. (decomp.) $C_{22}H_{23}N_5O_2$ (389.50) Calculated: C 67.85 H 5.95 N 17.98 Found: 67.62 5.90 17.74

(7) 5E-6-(3-(Cyanimido-piperidin-1-yl-methyleneamino)phenyl)-6-(3-pyridyl)hex-5-enoic acid Melting point: 197° C. (decomp. water/isopropanol) $C_{24}H_{27}N_5O_2 \times 0.5\ H_2O$ (417.51) Calculated: C 67.58 H 6.61 N 16.42 Found: 67.72 6.72 16.21

(8) 5E-6-(3-(2-Cyano-3-tert.butyl-guanidino)phenyl)-6-(3-pyridyl)hex-5-enoic acid Melting point: 150°–151° C. (decomp. ethanol/diiso-propylether) $C_{23}H_{27}N_5O_2$ (405.50) Calculated: C 68.12 H 6.71 N 17.27 Found: 67.94 6.78 17.08

(9) 5E-6-(3-(2-Cyano-3-cyclohexyl-guanidino)phenyl)-6-(3-pyridyl)hex-5-enoic acid Melting point: 156° C. (decomp. ethyl acetate/diethyl-ether) $C_{25}H_{29}N_5O_2$ (431.54) Calculated: C 69.58 H 6.77 N 16.23 Found: 69.38 5.80 16.06

(10) 5E-6-(3-(2-Cyano-3-cyclopentyl-guanidino)phenyl)-6-(3-pyridyl)hex-5-enoic acid Melting point: 136° C. (decomp. ethyl acetate/diethyl-ether) $C_{24}H_{27}N_5O_2$ (417.51) Calculated: C 69.04 H 6.57 N 16.77 Found: 68.96 6.48 16.61

(11) 5E-6-(3-(2-Cyano-3-isopropyl-guanidino)phenyl)-6-(3-pyridyl)hex-5-enoic acid Melting point: 186° C. (decomp. ethyl acetate/diethyl-ether) $C_{22}H_{25}N_5O_2$ (391.47) Calculated: C 67.50 H 6.44 N 17.89 Found: 67.31 6.50 17.71

(12) 5E-6-(3-(2-Cyano-3-(exo-norborn-2-yl)guanidino)phenyl)-6-(3-pyridyl)hex-5-enoic acid Melting point: 172°–173° C. (decomp. isopropanol/diisopropylether) $C_{26}H_{29}N_5O_2$ (443.55) Calculated: C 70.41 H 6.60 N 15.79 Found: 70.50 6.63 15.63

(13) 5E-6-(3-(Cyanimido-(3,3-dimethylpiperidin-1-yl)methyleneamino)phenyl)-6-(3-pyridyl)hex-5-enoic acid Melting point: 138° C. (decomp ethyl acetate/diiso-propylether) $C_{26}H_{31}N_5O_2$ (445.56) Calculated: C 70.09 H 7.01 N 15.72 Found: 69.98 7.10 15.59

(14) 5E-6-(3-(2-Cyano-3-trimethylsilylmethyl-guanidino)phenyl)-6-(3-pyridyl)hex-5-enoic acid Melting point: 92° C. (decomp. ethyl acetate/diethylether) $C_{23}H_{29}N_5O_2Si$ (435.60) Calculated: C 63.42 H 6.71 N 16.08 Found: 63.23 6.80 15.87

(15) 5E-6-(3-(2-Cyano-3-(3-pyridylmethyl)guanidino)phenyl)-6-(3-pyridyl)hex-5-enoic acid Melting point: 125°–126° C. (ethyl acetate/diiso-propylether) $C_{25}H_{24}N_6O_2$ (440.51) Calculated: C 68.17 H 5.49 N 19.08 Found: 67.96 5.52 18.93

(16) 5E-6-(3-(2-Cyano-3-(1,1,3,3-tetramethylbutyl)guanidino)phenyl)6-(3-pyridyl)hex-5-enoic acid Melting point: 170° C. (decomp. ethyl acetate/diiso-propylether) $C_{27}H_{35}N_5O_2$ (461.61) Calculated: C 70.25 H 7.64 N 15.17 Found: 70.25 7.73 15.12

(17) 5E-6-(3-(2-Cyano-3-(2-hydroxy-1-methyl-2-phenylethyl)guanidino)phenyl)-6-(3-pyridyl)hex-5-enoic acid Melting point: 152°–153° C. (ethyl acetate/diisopropylether) $C_{28}H_{29}N_5O_3$ (483.57) Calculated: C 69.55 H 6.05 N 14.49 Found: 69.43 6.16 14.38

(18) 5E-6-(3-(2-Cyano-3-(2-hydroxy-1-phenylethyl)guanidino)phenyl)- 6-(3-pyridyl)hex-5-enoic acid Foam, $R_f$ value: 0.33 (dichloromethane/ethanol=19:1) $C_{27}H_{27}N_5O_3$ (469.54) Calculated: C 69.07 H 5.80 N 14.92 Found: 68.98 5.87 14.80

(19) 5E-6-(3-(2-Cyano-3-methyl-3-isopropyl-guanidino)phenyl)-6-(3-pyridyl)hex-5-enoic acid Melting point: 168° C. (ethyl acetate/isopropanol) $C_{23}H_{27}N_5O_2$ (405.50) Calculated: C 68.13 H 6.71 N 17.27 Found: 68.03 6.74 17.33

(20) 5E-6-(3-(2-Cyano-3-benzyl-guanidino)phenyl)-6-(3-pyridyl)hex- 5-enoic acid Melting point: 138°–140 ° C. (ethyl acetate/tert.butylmethylether) $C_{26}H_{25}N_5O_2$ (439.52) Calculated: C 71.05 H 5.73 N 15.93 Found: 71.04 5.76 15.94

(21) 5E-6-(3-(2-Cyano-3-(2-methylpropyl)guanidino)-phenyl)-6-(3-pyridyl)hex-5-enoic acid Melting point: 129° C. (decomp., ethyl acetate/diisopropylether) $C_{23}H_{27}N_5O_2$ (405.50) Calculated: C 68.13 H 6.71 N 17.27 Found: 68.03 6.72 17.08

(22) 5E-6-(3-(2-Cyano-3-neopentyl-guanidino)phenyl)-6-(3-pyridyl)hex-5-enoic acid Melting point: 115°–116° C. (ethyl acetate/tert.butylmethylether) $C_{24}H_{29}N_5O_2$ (419.53) Calculated: C 68.71 H 6.97 N 16.69 Found: 68.53 7.07 16.53

(23) 5E-6-(3-(2-Cyano-3-pentyl-guanidino)phenyl)-6-(3-pyridyl)hex-5-enoic acid Melting point: 140°–142° C. (ethyl

(24) 5E-6-(3-(2-Cyano-3,3-dimethyl-guanidino)phenyl)-6-(3-pyridyl)hex-5-enoic acid Prepared as in Example 2b by reacting with dimethylamine in a bomb tube. Melting point: 194° C. (ethyl acetate/diisopropylether) $C_{21}H_{23}N_5O_2$ (377.45) Calculated: C 66.83 H 6.14 N 18.55 Found: 66.63 6.25 18.38

(25) 5E-6-(3-(2-Cyano-3-methyl-guanidino)phenyl)-6-(3-pyridyl)hex-5-enoic acid Prepared as in Example 2b by reacting with methylamine in a bomb tube. Melting point: 120° C. (ethyl acetate/isopropanol) $C_{20}H_{21}N_5O_2$ (363.42) Calculated: C 66.10 H 5.82 N 19.27 Found: 66.00 5.98 19.35

(26) 5E-6-(3-(2-Cyanoguanidino)phenyl)-6-(3-pyridyl)hex-5-enoic acid 2.2 g of methyl 6-(3-(2-cyanimido-phenoxymethyleneamino)phenyl)-6-(3-pyridyl)hex-5-enoate and 4.8 g of ammonium carbonate are stirred in 40 ml of methanol at ambient temperature for 72 hours. The reaction mixture is evaporated down and the residue is saponified in isopropanol by the addition of sodium hydroxide solution as in Example 2b. Melting point: 174° C. (ethyl acetate/isopropanol) $C_{19}H_{19}N_5O_2$ (349.39) Calculated: C 65.32 H 5.48 N 20.04 Found: 65.17 5.53 19.87

(27) 5E-6-(3-(Cyanimido-morpholin-1-yl-methyleneamino)phenyl)-6-(3-pyridyl)hex-5-enoic acid Melting point: 189° C. (water/isopropanol) $C_{23}H_{25}N_5O_3$ (4 19.49) Calculated: C 65.86 H 6.01 N 16.70 Found: 65.88 5.96 16.53

(28) 5E-6-(3-(2-Cyano-3-(2-dimethylaminoethyl)guanidino)phenyl)-6-(3-pyridyl)hex-5-enoic acid Foam, $R_f$ value: 0.28 (dichloromethane/methanol=9:1) $C_{23}H_{28}N_6O_2$ (420.51) Calculated: C 62.94 H 6.90 N 19.17 Found: 62.74 6.76 18.96

(29) 5E-6-(3-(2-Cyano-3-cyclohexylmethyl-guanidino)-phenyl)-6-(3-pyridyl)hex-5-enoic acid Melting point: 111° C. (ethyl acetate/isopropanol) $C_{26}H_{31}N_5O_2 \times 0.5$ ethyl acetate (445.57) Calculated: C 68.69 H 7.20 N 14.30 Found: 68.55 7.28 14.41

(30) 5E-6-(3-(2-Cyano-3-(3-methylbutyl)guanidino)-phenyl)-6-(3-pyridyl)hex-5-enoic acid Melting point: 108 ° C. (decomp., ethyl acetate/tert.butylmethylether) $C_{24}H_{29}N_5O_2$ (419.53) Calculated: C 68.71 H 6.97 N 16.69 Found: 68.67 7.09 16.73

(31) 5E-6-(3-(2-Cyano-3-methoxy-guanidino)phenyl)-6-(3-pyridyl)hex-5-enoic acid Melting point: 118° C. (decomp., ethyl acetate/isopropanol) $C_{20}H_{21}N_5O_3$ (379.42) Calculated: C 63.31 H 5.58 N 18.46 Found: 63.19 5.53 18.28

(32) 5E-6-(3-(2-Cyano-3-methoxy-3-methyl-guanidino)phenyl)-6-(3-pyridyl)hex-5-enoic acid Melting point: 116° C. (ethyl acetate/diisopropylether) $C_{21}H_{23}N_5O_3$ (393.45) Calculated: C 64.11 H 5.89 N 17.80 Found: 64.21 5.85 17.62

(33) E/Z-5-(3-(2-Cyano-3-(2-methylpropyl)guanidino)phenyl)-5-(3-pyridyl)pent-4-enoic acid Melting point: 189° C. (ethyl acetate/diisopropylether) $C_{22}H_{25}N_5O_2$ (391.47) Calculated: C 67.50 H 6.44 N 17.89 Found: 67.31 6.48 17.79

(34) E/Z-5-(3-(2-Cyano-3-tert.butyl-guanidino)phenyl)-5-(3-pyridyl)pent-4-enoic acid Melting point: 146°–148° C. (ethyl acetate/isopropanol) $C_{22}H_{25}N_5O_2$ (391.47) Calculated: C 67.50 H 6.44 N 17.89 Found: 67.32 6.50 17.68

(35) 6E-7-(3-(2-Cyano-3-cyclopropyl-guanidino)phenyl)-7-(3-pyridyl)hept-6-enoic acid Foam, $R_f$ value: 0.24 (silica gel; dichloromethane/ethanol=20:1) $C_{23}H_{25}N_5O_2$ (403.49) Calculated: C 68.47 H 6.25 N 17.36 Found: 68.40 6.39 17.20

(36) 6E-7-(3-(2-Cyano-3-cyclohexyl-guanidino)phenyl)-7-(3-pyridyl)hept-6-enoic acid Foam, $R_f$ value: 0.26(silica gel; dichloromethane/ethanol=20:1) $C_{26}H_{31}N_5O_2$ (445.56) Calculated: C 70.09 H 7.01 N 15.72 Found: 70.17 7.05 15.52

(37) 6E-7-(3-(2-Cyano-3-tert.butyl-guanidino)phenyl)-7-(3-pyridyl)hept-6-enoic acid Melting point: 96° C. (ethyl acetate/diisopropylether) $C_{24}H_{29}N_5O_2$ (419.53) Calculated: C 68.71 H 6.97 N 16.69 Found: 68.54 7.08 16.44

(38) 7E-8-(3-(2-Cyano-3-(2-methylpropyl)guanidino)phenyl)-8-(3-pyridyl)oct-7-enoic acid Foam, $R_f$ value: 0.62 (silica gel; dichloromethane/ethanol=9:1) $C_{25}H_{31}N_5O_2$ (433.55) Calculated: C 69.26 H 7.21 N 16.15 Found: 69.14 7.30 15.99

(39) 7E-8-(3-(2-Cyano-3-tert.butyl-guanidino)phenyl)-8-(3pyridyl)oct-7-enoic acid Melting point: 136°–138° C. (ethyl acetate) $C_{25}H_{31}N_5O_2$ (433.55) Calculated: C 69.26 H 7.21 N 16.15 Found: 69.04 7.15 16.17

(40) E/Z-6-(3-(2-Cyano-3-cyclopropyl-1-methylguanidino)phenyl)-6-(3-pyridyl)hex-5-enoic acid Melting point: 158°–160° C. (ethyl acetate/isopropanol) $C_{23}H_{25}N_5O_2$ (403.49) Calculated: C 68.47 H 6.25 N 17.36 Found: 68.34 5.25 17.26

(41) 5E-6-(3-(2-Cyano-3-cyclopropyl-guanidino)-4methylphenyl)-6-(3-pyridyl)hex-5-enoic acid Melting point: 156°–158° C. (ethyl acetate/diiso-propylether) $C_{25}H_{29}N_5O_2$ (431.54) Calculated: C 69.58 H 6.77 N 16.23 Found: 69.39 6.93 16.29

(42) 5E-6-(3-(2-Cyano-3-neopentyl-guanidino)-4-methylphenyl)-6-(3-pyridyl)hex-5-enoic acid Melting point: 148°–149° C. (ethyl acetate/diiso-propylether) $C_{25}H_{31}N_5O_2$ (433.55) Calculated: C 69.26 H 7.21 N 16.15 Found: 69.08 7.33 16.24

(43) 5E-6-(3-(2-Cyano-3-propyl-guanidino)-4-methylphenyl)-6-(3-pyridyl)hex-5-enoic acid Melting point: 169°–171° C. (ethyl acetate/diiso-propylether) $C_{23}H_{27}N_5O_2$ (405.50) Calculated: C 68.13 H 6.71 N 17.27 Found: 67.95 6.87 17.24

(44) 5E-6-(3-(3-tert.butyl-2-cyano-guanidino)-4-methylphenyl)-6-(3-pyridyl)hex-5-enoic acid Melting point: 127°–129° C. (ethyl acetate/diiso-propylether) $C_{24}H_{29}N_5O_2$ (419.53) Calculated: C 68.71 H 6.97 N 16.69 Found: 68.56 7.05 16.84

(45) 5E-6-(3-(2-Cyano-3-cyclopentyl-guanidino)-5-trifluoromethylphenyl)-6-(3-pyridyl)hex-5-enoic acid Melting point: 152° C. (ethyl acetate/diisopropylether) $C_{25}H_{26}F_3N_5O_2$ (485.51) Calculated: C 61.85 H 5.40 N 14.42 Found: 61.73 5.50 14.48

(46) 5E-6-(3-(2-Cyano-3-(2-methylpropyl)guanidino)-5-trifluoromethylphenyl)-6-(3-pyridyl)hex-5-enoic acid Melting point: 164° C. (ethyl acetate) $C_{24}H_{26}F_3N_5O_2$ (473.50) Calculated: C 60.88 H 5.53 N 14.79 Found: 60.69 5.47 14.88

(47) 5E-6-(3-(2-Cyano-3-(exo-norborn-2-yl)guanidino)-5-trifluoromethylphenyl)-6-(3-pyridyl)hex-5-enoic acid Melting point: 144°–145° C. (ethyl acetate) $C_{27}H_{28}F_3N_5O_2$ (511.55) Calculated: C 63.39 H 5.42 N 13.69 Found: 63.25 5.49 13.58

(48) 5E-6-(3-(2-Cyano-3-cycloheptyl-guanidino)phenyl)-6-(3-pyridyl)hex-5-enoic acid Melting point: 178 ° C. (decomp., ethyl acetate/diisopropyl ether) $C_{26}H_{31}N_5O_2$ (445.57) Calculated: C 70.09 H 7.01 N 15.72 Found: 69.96 7.08 15.52

(49) 5E-6-(3-(2-Cyano-3-cyclooctyl-guanidino)phenyl)-6-(3-pyridyl)hex-5-enoic acid Melting point: 154° C. (decomp., ethyl acetate/diisopropyl ether) $C_{27}H_{33}N_5O_2$ (459.59) Calculated: C 70.56 H 7.24 N 15.24 Found: 70.39 7.18 15.14

(50) 5E-6-(3-(3-(Adamant-1-yl)-2-cyano-guanidino)phenyl)-6-(3-pyridyl)hex-5-enoic acid Melting point: 148° C. (decomp., isopropanol/water) $C_{29}H_{33}N_5O_2$ (483.61) Calculated: C 72.02 H 6.88 N 14.48 Found: 71.86 6.85 14.45

Example 3

6-(3-(2-Cyano-3-isopropyl-guanidino)phenyl)-6-(3-pyridyl)hexanoic acid a) 6-(3-Acetylaminophenyl)-6-(3-pyridyl)hexanoic acid 9.75 g of 6-(3-acetylaminophenyl)-6-(3-pyridyl)hex-5-enoic acid are dissolved in 33 ml of 1N sodium hydroxide solution and after the addition of 1 g of 10% palladium/charcoal the solution is hydrogenated at ambient temperature under 5 bar of hydrogen for one hour. Then the catalyst is filtered off, the filtrate is adjusted to pH 4–5 by the addition of citric acid and concentrated by evaporation. The residue is decocted three times with methanol/ethanol (9:1). The combined organic extracts are evaporated down and the residue is purified over a silica gel column with dichloromethane/methanol=19:1.

Yield: 73% of theory, Foam, $R_f$ value: 0.72 (silica gel; dichloromethane/methanol=9:1) $C_{19}H_{22}N_2O_3$ (326.40) Calculated: C 69.92 H 6.79 N 8.58 Found: 69.70 6.72 8.43 b) Methyl 6-(3-Aminophenyl)-6-(3-pyridyl)hexanoate 6.9 g of 6-(3-acetylaminophenyl)-6-(3-pyridyl)hexanoic acid are stirred in 40 ml of 9N methanolic hydrochloric acid for 24 hours at ambient temperature. The reaction solution is evaporated down, the residue is taken up in water and made alkaline by the addition of sodium carbonate. The aqueous phase is extracted with ethyl acetate. The organic extract is washed with water, dried and evaporated down.

Yield: 81% of theory, Oil, $R_f$ value: 0.52 (silica gel; dichloromethane/ethanol=9:1) $C_{18}H_{22}N_2O_2$ (298.38) Calculated: C 72.46 H 7.43 N 9.39 Found: 72.28 7.58 9.23 c) Methyl 6-(3-cyanimido-phenoxymethyleneamino)phenyl)6-(3-pyridyl)hexanoate 5.1 g of methyl 6-(3-aminophenyl)-6-(3-pyridyl)hexanoate and 4.1 g of diphenoxymethylenecyanamide are stirred in 130 ml of isopropanol for 4 days at ambient temperature. The reaction mixture is evaporated down and the residue is purified over a silica gel column with dichloromethane/ethanol=19:1.

Yield: 91% of theory, Resin, $R_f$ value: 0.54 (silica gel; dichloro-methane/ethanol=19:1) $C_{26}H_{26}N_4O_3$ (442.52) Calculated: C 70.57 H 5.92 N 15.66 Found: 70.41 6.03 15.68 d) 6-(3-(2-Cyano-3-isopropyl-guanidino)phenyl)-6-(3-pyridyl)hexanoic acid 3.1 g of methyl 6-(3-cyanimido-phenoxymethyleneamino)-phenyl)6-(3-pyridyl)hexanoate and 5 ml of isopropylamine are refluxed for 3 hours in 50 ml of isopropanol. Then, at 50° C., 10 ml of 2N sodium hydroxide solution are added and the reaction solution is stirred for 30 minutes at this temperature. It is then evaporated down, the residue is taken up in water and washed with ethyl acetate. The aqueous phase is adjusted to pH 4–5 by the addition of citric acid, the precipitate formed is suction filtered and recrystallised from ethyl acetate/isopropanol.

Yield: 64% of theory, Melting point: 168°–169° C. $C_{22}H_{27}N_5O_2$ (393.49) Calculated: C 67.15 H 6.92 N 17.80 Found: 67.12 6.95 17.87

The following compound is obtained analogously to Example 3:

6-(3-(2-Cyano-3-tert.butyl-guanidino)phenyl)-6-(3-pyridyl)hexanoic acid Melting point: 142° C. (ethyl acetate/isopropanol) $C_{23}H_{29}N_5O_2$ ((407.51) Calculated: C 67.79 H 7.17 N 17.19 Found: 67.62 7.25 17.07

Example 4

5E-6-(3-(1-Neopentylamino-2-nitro-ethyleneamino)phenyl)-6-(3-pyridyl)hex- 5-enoic acid a) Methyl 5E-6-(3-(1-methylthio-2-nitro-ethyleneamino)phenyl)-6-(3pyridyl)hex-5-enoate 3 g of methyl 5E-6-(3-aminophenyl)-6-(3-pyridyl)hex-5-enoate and 1.65 g of 1,1-bis-(methylthio)-2-nitroethene are refluxed for 20 hours in 50 ml of isopropanol. The reaction mixture is filtered, the filtrate is concentrated by evaporation and the residue is purified over a silica gel column using dichloromethane/ethanol=30:1. The product fraction is evaporated down and the residue is recrystallised from tert.butylmethylether.

Yield: 63% of theory, Melting point: 84° C. $C_{21}H_{23}N_3O_4S$ (413.50) Calculated: C 61.00 H 5.61 N 10.16 S 7.75 Found: 60.99 5.52 10.23 7.62 b) 5E-6-(3-(1-Neopentylamino-2-nitro-ethyleneamino)phenyl)-6-(3-pyridyl)hex-5-enoic acid 2.1 g of methyl 5E-6-(3-(1-methylthio-2-nitro-ethyleneamino)phenyl)- 6-(3-pyridyl)hex-5-enoate and 2.4 ml of neopentylamine are refluxed for 5 hours in 20 ml of isopropanol. At 60° C. the reaction mixture is combined with 10 ml of 2N sodium hydroxide solution and stirred for 30 minutes at this temperature. Then the reaction solution is evaporated down, the residue is taken up in water and the aqueous phase is washed with ethyl acetate. The aqueous phase is adjusted to pH 4–5 by the addition of citric acid and extracted with ethyl acetate. The organic extract is evaporated down and the residue is recrystallised from water/isopropanol.

Yield: 70% of theory, Melting point: 190°–191° C. $C_{24}H_{30}N_4O_4$ (438.53) Calculated: C 65.73 H 6.90 N 12.78 Found: 65.62 6.98 12.61

The following compound is obtained analogously to Example 4:

5E-6-(3-(1-Cyclohexylamino-2-nitro-ethyleneamino)-phenyl)-6-(3-pyridyl)hex-5-enoic acid Melting point: 155°–157° C. (ethyl acetate/isopropanol) $C_{25}H_{30}N_4O_4$ (450.54) Calculated: C 66.65 H 6.71 N 12.44 Found: 66.61 6.71 12.39

Example 5

5E-6-(3-(2,2-Dicyano-(2-methylpropylamino)ethyleneamino)phenyl)-6-(3-pyridyl)hex-5-enoic acid a) Methyl 5E-6-(3-(2,2-dicyano-1-methylthioethyleneamino)phenyl)6-(3-pyridyl)hex-5-enoate 13.4 g of methyl 5E-6-(3-aminophenyl)-6-(3-pyridyl)-hex-5-enoate and 7.7 g of 2,2-dicyano-1,1-bis(methylthio)ethene are refluxed for 6 hours in 130 ml of isopropanol. The reaction mixture is evaporated down and the residue is recrystallised from ethyl acetate/diisopropylether.

Yield: 45% of theory, Melting point: 125°–127° C. $C_{23}H_{22}N_4O_2S$ (418.51) Calculated: C 66.01 H 5.30 N 13.39 S 7.66 Found: 65.97 5.27 13.49 7.66 b) 5E-6-(3-(2,2-dicyano-1-(2-methylpropylamino)ethyleneamino)phenyl)-6-(3-pyridyl)hex-5-enoic acid 4 g of methyl 5E-6-(3-(2,2-dicyano-1-methylthioethyleneamino)phenyl)-6-(3-pyridyl)hex-5-enoate and 10 ml of 2-methylpropylamine are refluxed for 4 hours in 80 ml of isopropanol. The reaction mixture is combined at 40° C. with 10 ml of 2N sodium hydroxide solution and stirred for one hour at this temperature. It is then evaporated down, the residue is taken up in water and washed with ethyl acetate. The aqueous phase is adjusted to pH 4–5 by the addition of citric acid and extracted with ethyl acetate. The organic extract is concentrated by evaporation and the residue is purified over a silica gel column with dichloromethane/ethanol=29:1.

Yield: 68% of theory, Foam, $R_f$ value: 0.48 (silica gel; dichloromethane/ethanol=19:1) $C_{25}H_{27}N_5O_2$ (429.52) Calculated: C 69.91 H 6.34 N 16.30 Found: 69.70 6.23 16.16

The following compounds are obtained analogously to Example 5:

(1) 5E-6-(3-(2,2-Dicyano-1-isopropylaminoethyleneamino)phenyl)-6-(3-pyridyl)hex-5-enoic acid Melting point: 164°–165° C. (ethyl acetate/diethylether) $C_{24}H_{25}N_5O_2$ (415.49) Calculated: C 69.38 H 6.06 N 16.86 Found: 69.22 6.11 16.68

(2) 5E-6-(3-(2,2-Dicyano-1-(3-methylbutylamino)ethyleneamino)phenyl)-6-(3-pyridyl)hex-5-enoic acid Melting point: 139° C. (ethyl acetate/diisopropylether) $C_{26}H_{29}N_5O_2$ (443.55) Calculated: C 70.41 H 6.59 N 15.79 Found: 70.47 6.72 15.61

(3) 5E-6-(3-(2,2-Dicyano-1-cyclopentylaminoethyleneamino)phenyl)-6-(3-pyridyl)hex-5-enoic acid Melting point: 150° C. (ethyl acetate/diisopropylether) $C_{26}H_{27}N_5O_2$ (441.53) Calculated: C 70.73 H 6.16 N 15.86 Found: 70.55 6.27 15.90

(4) 5E-6-(3-(2,2-Dicyano-1-neopentylaminoethyleneamino)phenyl)-6-(3-pyridyl)hex-5-enoic acid Melting point: 116° C. (ethyl acetate/diisopropylether) $C_{26}H_{29}N_5O_2$ (443.55) Calculated: C 70.41 H 6.59 N 15.79 Found: 70.29 6.63 15.65

(5) 5E-6-(3-(2,2-Dicyano-1-cyclopropylaminoethyleneamino)phenyl)-6-(3-pyridyl)hex-5-enoic acid Melting point: 173 ° C. (ethyl acetate/tert.-butylmethylether) $C_{24}H_{23}N_5O_2$ (413.48) Calculated: C 69.72 H 5.61 N 16.94 Found: 69.57 5.77 17.05

(6) 5E-6-(3-(2,2-Dicyano-1-benzylamino-ethyleneamino)phenyl)6-(3-pyridyl)hex-5-enoic acid Melting point: 154° C. (isopropanol/water) $C_{28}H_{25}N_5O_2$ (463.54) Calculated: C 72.55 H 5.44 N 15.11 Found: 72.42 5.59 15.02

(7) 5E-6-(3-(2,2-Dicyano-1-propylamino-ethyleneamino)phenyl)6-(3-pyridyl)hex-5-enoic acid Melting point: 116° C. (ethyl acetate/diisopropylether) $C_{24}H_{25}N_5O_2$ (415.49) Calculated: C 69.38 H 6.06 N 16.86 Found: 69.25 6.13 16.77

(8) 5E-6-(3-(2,2-Dicyano-1-methylamino-ethyleneamino)phenyl)-6-(3-pyridyl)hex-5-enoic acid Prepared analogously to Example 5b by reacting with methylamine in a bomb tube. Melting point: 178° C. (ethyl acetate) $C_{22}H_{21}N_5O_2$ (387.44) Calculated: C 68.20 H 5.46 N 18.08 Found: 68.10 5.58 18.12

(9) 5E-6-(3-(2,2-Dicyano-1-dimethylaminoethyleneamino)phenyl)- 6-(3-pyridyl)hex-5-enoic acid Prepared analogously to Example 5b by reacting with dimethylamine in a bomb tube. Melting point: 147° C. (ethyl acetate) $C_{23}H_{23}N_5O_2$ (401.47) Calculated: C 68.81 H 5.77 N 17.44 Found: 68.75 5.83 17.28

(10) 5E-6-(3-(2,2-Dicyano-1-(exo-norborn-2-ylamino)ethyleneamino)phenyl)- 6-(3-pyridyl)hex-5-enoic acid Melting point: 154°–156° C. (tert.butylmethylether) $C_{28}H_{29}N_5O_2$ (467.57) Calculated: C 71.93 H 6.25 N 14.98 Found: 71.81 6.31 14.87

(11) 5E-6-(3-(2,2-Dicyano-1-cyclooctylaminoethyleneamino)phenyl)- 6-(3-pyridyl)hex-5-enoic acid Melting point: 167°–169° C. (ethyl acetate) $C_{29}H_{33}N_5O_2$ (483.61) Calculated: C 72.02 H 6.88 N 14.48 Found: 72.00 6.94 14.40

(12) 5E-6-(3-(2,2-Dicyano-1-cycloheptylaminoethyleneamino)phenyl)- 6-(3-pyridyl)hex-5-enoic acid Melting point: 140°–142° C. (ethyl acetate) $C_{28}H_{31}N_5O_2$ (469.59) Calculated: C 71.62 H 7.07 N 14.91 Found: 71.49 7.16 14.84

(13) 5E-6-(3-(2,2-Dicyano-1-cyclopentylamino-ethyleneamino)-5-trifluoromethyl-phenyl)- 6-(3-pyridyl)hex-5-enoic acid Melting point: 118° C. (ethyl acetate/diisopropylether) $C_{27}H_{28}F_3N_5O_2$ (509.54) Calculated: C 63.65 H 5.14 N 13.74 Found: 63.50 5.25 13.57

Example 6

5E-6-(3-(2,2-Dicyano-1-tert.butylamino-ethyleneamino)-phenyl)-6-(3-pyridyl)hex-5-enoic acid 2.1 g of methyl 5E-6-(3-(2,2-dicyano-1-methylthioethyleneamino)phenyl)- 6-(3-pyridyl)-hex-5-enoate are dissolved in 100 ml of dichloromethane. 1.9 g of 3-chloroperbenzoic acid are added and the mixture is stirred for one hour at ambient temperature. Then the reaction mixture is combined with 10 ml of tert.butylamine and stirred for 12 hours at ambient temperature. The reaction mixture is washed with water, evaporated down, the residue is taken up in 20 ml of ethanol and 20 ml of 1N sodium hydroxide solution and heated to 50° C. for 3 hours. The reaction solution is evaporated down, the residue is taken up in water and washed with ethyl acetate. The aqueous phase is adjusted to pH 4–5 by the addition of citric acid and extracted with ethyl acetate. The organic phase is evaporated down and the residue is purified over a silica gel column with dichloromethane/ethanol=20:1. The product fraction is evaporated down and the residue is recrystallised from ethyl acetate/diisopropylether.

Yield: 43% of theory, Melting point: 188°–189° C. $C_{25}H_{27}N_5O_2$ (429.52) Calculated: C 69.91 H 6.34 N 16.30 Found: 69.71 6.37 16.18

The following compounds are obtained analogously to Example 6

(1) 5E-6-(3-(1-Adamant-1-ylamino-2,2-dicyanoethyleneamino)phenyl)- 6-(3-pyridyl)hex-5-enoic acid Melting point: 142° C. (decomp., isopropanol/diisopropyl-ether) $C_{31}H_{33}N_5O_2$ (507.64) Calculated: C 73.35 H 6.55 N 13.80 Found: 73.22 6.61 13.71

(2) 5E-6-(3-(2,2-Dicyano-1-diethylamino-ethyleneamino)phenyl)-6-(3-pyridyl)hex-5-enoic acid Melting point: 167°–168° C. (ethyl acetate/diiso-propylether) $C_{25}H_{27}N_5O_2$ (429.52) Calculated: C 69.91 H 6.34 N 16.30 Found: 69.73 6.46 16.24

Example 7

E/Z-6-(4-(2-(2-Cyano-3-tert.butyl-guanidino)ethyl)-phenyl)-6-(3-pyridyl)hex-5-enoic acid a) Methyl E/Z-6-(4-(2-(cyanimido-phenoxymethyleneamino)ethyl)phenyl)- 6-(3-pyridyl)hex-5-enoate 26.5 g of E/Z-6-(4-(2-(acetylamino)ethyl)phenyl)-6-(3-pyridyl)-hex-5-enoic acid are refluxed for 12 hours in 200 ml of 6N hydrochloric acid. The reaction solution is evaporated down, the residue is taken up in 200 ml of 3N methanolic hydrochloric acid and stirred for 12 hours at ambient temperature. The reaction solution is evaporated down, the residue is dissolved in water and washed with ethyl acetate. The aqueous phase is made alkaline at 0° C. by the addition of conc. ammonia and extracted with dichloromethane. The organic extract is washed with water, dried and evaporated down. The residue is stirred for 14 hours at ambient temperature together with 14.9 g of diphenoxymethylenecyanamide in 300 ml of isopropanol. The solvent is eliminated and the residue is purified over a silica gel column with dichloromethane/ethanol=30:1.

Yield: 80% of theory, Oil, $R_f$ value: 0.72 (silica gel; dichloromethane/ethanol=20:1) $C_{28}H_{28}N_4O_3$ (468.56) Calculated: C 71.78 H 6.02 N 11.96 Found: 71.64 6.08 11.85 b) E/Z-6-(4-(2-(2-Cyano-3-tert.butyl-guanidino)ethyl)phenyl)-6-(3-pyridyl)hex- 5-enoic acid 2.35 g of methyl E/Z-6-(4-(2-(cyanimido-phenoxymethyleneamino)ethyl)phenyl)- 6-(3-pyridyl)hex-5-enoate and 3 ml of tert.butylamine are refluxed for 3 hours in 40 ml of isopropanol. Then the reaction mixture is combined with 10 ml of 2N sodium hydroxide solution at 50° C. and stirred at this temperature for 30 minutes. The reaction mixture is evaporated down, the residue is taken up in water and washed with ethyl acetate. The aqueous phase is adjusted to pH 4–5 by the addition of citric acid and extracted with ethyl acetate. The organic extract is washed with water, evaporated down and the residue is purified over a silica gel column with dichloromethane/ethanol=20:1.

Yield: 55% of theory, Foam, $R_f$ value: 0.64 (dichloromethane/ethanol=9:1) $C_{25}H_{31}N_5O_2$ (433.55) Calculated: C 69.26 H 7.21 N 16.15 Found: 69.27 7.29 15.95

The following compound is obtained analogously to Example 7:

E/Z-6-(4-(2-(2-Cyano-3-(2-methylpropyl)guanidino)ethyl)phenyl)- 6-(3-pyridyl)hex-5-enoic acid Resin, $R_f$ value: 0.48 (dichloromethane/ethanol=9:1) $C_{25}H_{31}N_5O_2$ (433.55) Calculated: C 69.26 H 7.21 N 16.15 Found: 69.17 7.26 16.17

Example 8

5E-6-(3-(2,2-Dicyano-1-(2-methylpropylamino)ethyleneamino)phenyl)- 6-(3-pyridyl)hex-5-enoic acid methylamide 1.1 g of 5E-6-(3-(2,2-dicyano-1-(2-methylpropylamino)ethyleneamino)phenyl)-6-( 3-pyridyl)hex-5-enoic acid are dissolved in 20 ml of absolute tetrahydrofuran. 0.5 g of carbonyldiimidazole are added thereto, the mixture is stirred until the development of gas has died away and then 0.09 g of methylamine are added. The reaction mixture is stirred for 12 hours at ambient temperature, then mixed with 2 ml of water and evaporated down. The residue is taken up in ethyl acetate. The organic extract is washed with water, dried, evaporated down and the residue is purified over a silica gel column with dichloromethane/ethanol=14:1.

Yield: 60% of theory, Foam, $R_f$ value: 0.61 (silica gel; dichloromethane/ethanol=9:1) $C_{26}H_{30}N_6O$ (442.56) Calculated: C 70.56 H 6.83 N 18.99 Found: 70.39 6.86 18.82

The following compounds are obtained analogously to Example 8:

(1) 5E-6-(3-(2,2-Dicyano-1-(2-methylpropylamino)ethyleneamino)phenyl)- 6-(3-pyridyl)hex-5-enoic acid methylamide Foam, $R_f$ value: 0.63 (silica gel; dichlormethane/ethanol=9:1) $C_{27}H_{32}N_6O$ (456.59) Calculated: C 71.03 H 7.06 N 18.41 Found: 70.83 7.17 18.43

(2) Methyl 5E-6-(3-(2,2-dicyano-1-(2-methylpropylamino)ethyleneamino)phenyl)- 6-(3-pyridyl)hex-5-enoate Melting point: 127°–129° C. (tert.butylmethylether) $C_{26}H_{29}N_5O_2$ (443.55) Calculated: C 70.41 H 6.59 N 15.79 Found: 70.45 6.62 15.83

(3) Methyl 5E-6-(3-(2,2-dicyano-1-isopropylaminoethyleneamino)phenyl)- 6-(3-pyridyl)hex-5-enoate Melting point: 159° C. (diisopropylether) $C_{25}H_{27}N_5O_2$ (429.52) Calculated: C 69.91 H 6.34 N 16.31 Found: 69.87 6.41 16.48

(4) (2-Methylpropyl) 5E-6-(3-(2,2-dicyano-1-isopropylaminoethyleneamino)phenyl)-6-(3-pyridyl)hex-5-enoate Oil, $R_f$ value: 0.53 (silica gel; dichloromethane/ethanol= 20:1) $C_{28}H_{33}N_5O_2$ (471.61) Calculated: C 71.31 H 7.05 N 14.85 Found: 71.10 7.16 15.09

(5) Isopropyl 5E-6-(3 -(2,2-dicyano-1-isopropylaminoethyleneamino)phenyl)-6-(3-pyridyl)hex-5-enoate Melting point: 119 ° C. (ethyl acetate/diisopropylether) $C_{27}H_{31}N_5O_2$ (457.58) Calculated: C 70.87 H 6.83 N 15.31 Found: 70.65 6.99 15.35

(6) Methyl 5E-6-(3-(2-cyano-3-(2-methylpropyl)guanidino)phenyl)-6-(3 -pyridyl)hex-5-enoate Oil, $R_f$ value: 0.35 (silica gel; dichloromethane/ethanol=20:1) $C_{24}H_{29}N_5O_2$ (419.53) Calculated: C 68.71 H 6.97 N 16.69 Found: 68.52 7.12 16.50

(7) (2-Methylpropyl) 5E-6-(3-(2-cyano-3-(2methylpropyl)guanidino)phenyl)-6-(3-pyridyl)hex-5-enoate Oil, $R_f$ value: 0.38 (silica gel; dichloromethane/ethanol=20:1) $C_{27}H_{35}N_5O_2$ (461.61) Calculated: C 70.25 H 7.64 N 15.17 Found: 70.04 7.78 14.98

(8) Isopropyl 5E-6-(3-(2-cyano-3-(2-methylpropyl)guanidino)phenyl)-6-(3-pyridyl)hex-5-enoate Oil, $R_f$ value: 0.37 (silica gel; dichloromethane/ethanol=20:1) $C_{26}H_{33}N_5O_2$ (447.58) Calculated: C 69.77 H 7.43 N 15.65 Found: 69.65 7.55 15.51

(9) 5E-6-(3-(2,2-dicyano-1-isopropylaminoethyleneamino)phenyl)-6-(3-pyridyl)hex-5-enoic acid amide Melting point: 123° C. (ethyl acetate/diisopropylether) $C_{24}H_{26}N_6O$ (414.50) Calculated: C 69.55 H 6.32 N 20.28 Found: 69.46 6.43 20.42

(10) Cyclohexyl 5E-6-(3-(2-cyano-3-(2-methylpropyl)guanidino)phenyl)-6-(3-pyridyl)hex-5-enoate Oil, $R_f$ value: 0.42 (silica gel; dichloromethane/ethanol=20:1) $C_{29}H_{37}N_5O_2$ (487.65) Calculated: C 71.43 H 7.65 N 14.36 Found: 71.38 7.68 14.18

Example 9

5E-6-(3-(3-Neopentyl-2-phenylsulphonyl-guanidino)phenyl)-6-(3-pyridyl)hex- 5-enoic acid a) Diphenoxymethylene-phenylsulphonamide 13.5 g of dichloro-diphenoxymethane and 17.3 g of phenylsulphonamide are refluxed for 48 hours in 160 ml of ethyl acetate. The reaction mixture is evaporated down, the residue is taken up in water and adjusted to pH 8 by the addition of sodium hydrogen carbonate. The aqueous phase is extracted with ethyl acetate. The organic extract is evaporated down, the residue is heated in dichloromethane and filtered. The filtrate is evaporated down and the residue is purified over a silica gel column with dichloromethane. The product fraction is evaporated down and the residue is recrystallised from ethyl acetate/diisopropylether.

Yield: 26% of theory, Melting point: 121°–122° C. $C_{19}H_{15}NO_4S$ (353.40) Calculated: C 64.58 H 4.28 N 3.96 S 9.07 Found: 64.60 4.41 3.94 8.94

The following compound is obtained analogously to Example 9a

Diphenoxymethylene-methylsulphonamide Melting point: 124° C. (ethyl acetate/diisopropylether) $C_{14}H_{13}NO_4S$ (291.33) Calculated: C 57.72 H 4.50 N 4.81 S 11.01 Found: 57.62 4.58 4.87 11.10 b) Methyl 5E-6-(3-(phenylsulphonimido-phenoxymethyleneamino)phenyl-6-(3-pyridyl)hex-5-enoate 3.5 g of diphenoxymethylene-phenylsulphonamide and 3 g of methyl 5E-6-(3-aminophenyl)-6-(3-pyridyl)hex-5-enoate are stirred in 60 ml of isopropanol for 48 hours at ambient temperature. The reaction mixture is evaporated down and the residue is purified over a silica gel column with dichloromethane. The product fraction is evaporated down and the residue is recrystallised from diethylether/ petroleum ether.

Yield: 86% of theory, Melting point: 90°–92° C. $C_{31}H_{29}N_3O_5S$ (555.65) Calculated: C 67.01 H 5.26 N 7.56 S 5.77 Found: 66.82 5.35 7.63 5.81

The following compound is obtained analogously to Example 9b:

Methyl 5E-6-(3-(methylsulphonimido-phenoxymethyleneamino)phenyl)-6-(3-pyridyl)hex-5-enoate Melting point: 101°–102° C. (ethyl acetate/petroleum ether) $C_{26}H_{27}N_3O_5S$ (493.58) Calculated: C 63.27 H 5.51 N 8.51 S 6.50 Found: 63.39 5.58 8.56 6.59 c) 5E-6-(3-(3-Neopentyl-2-phenylsulphonyl-guanidino)phenyl)-6(3-pyridyl)hex-5-enoic acid 2.4 g of methyl 5E-6-(3-phenylsulphonimidophenoxymethyleneamino)phenyl)-6-(3-pyridyl)hex-5-enoate and 2.4 ml of neopentylamine are refluxed for one hour in 40 ml of isopropanol. The mixture is left to cool to 50° C., the reaction mixture is combined with 10 ml of 2N sodium hydroxide solution and stirred for 30 minutes at 50° C. The reaction mixture is evaporated down, the residue is taken up in water and extracted with ethyl acetate. The aqueous phase is adjusted to pH 4–5 by the addition of citric acid and extracted with ethyl acetate. The organic extract is evaporated down and the residue is recrystallised from ethyl acetate/isopropanol.

Yield: 91% of theory, Melting point: 159°–160° C. $C_{29}H_{34}N_4O_4S$ (534.68) Calculated: C 65.15 H 6.41 N 10.48 S 6.00 Found: 65.05 6.52 10.48 6.04

The following compounds are obtained analogously to Example 9c:

(1) 5E-6-(3-(3-tert.butyl-2-phenylsulphonyl-guanidino)phenyl)-6-(3-pyridyl)hex-5-enoic acid Foam, $R_f$ value: 0.20 (dichloromethane/ethanol=30:1) $C_{28}H_{32}N_4O_4S$ (520.65) Calculated: C 64.59 H 6.19 N 10.76 S 6.16 Found: 64.39 6.27 10.61 6.13

(2) 5E-6-(3-(3-(2-methylpropyl)-2-phenylsulphonylguanidino)phenyl)-6-(3-pyridyl)hex-5-enoic acid Melting point: 124°–125° C. (ethyl acetate) $C_{28}H_{32}N_4O_4S$ (520.65) Calculated: C 64.59 H 6.19 N 10.76 S 6.16 Found: 64.45 6.24 10.59 6.11

(3) 5E-6-(3-(3-neopentyl-2-methylsulphonyl-guanidino)phenyl)-6-(3-pyridyl)hex-5-enoic acid Melting point: 143°–144° C. (ethyl acetate/isopropanol) $C_{24}H_{32}N_4O_4S$ (472.61) Calculated: C 60.99 H 6.83 N 11.86 S 6.78 Found: 60.87 6.95 11.79 6.73

(4) 5E-6-(3-(3-(2-Methylpropyl)-2-methylsulphonylguanidino)phenyl)-6-(3-pyridyl)hex-5-enoic acid Melting point: 158° C. (ethyl acetate/isopropanol) $C_{23}H_{30}N_4O_4S$ (458.58) Calculated: C 60.24 H 6.59 N 12.22 S 6.99 Found:60.15 6.65 12.08 6.92

(5) 5E-6-(3-(3-Cyclopentyl-2-methylsulphonylguanidino)phenyl)-6-(3-pyridyl)hex-5-enoic acid Melting point: 169°–170° C. (ethyl acetate/isopropanol) $C_{24}H_{30}N_4O_4S$ (470.59) Calculated: C 61.26 H 6.43 N 11.91 S 6.81 Found: 61.41 6.45 12.10 6.90

(6) 5E-6-(3-(3-tert.butyl-2-methylsulphonyl-guanidino)phenyl)-6-(3-pyridyl)hex-5-enoic acid Melting point: 150°–151° C. (ethyl acetate/diiso-propylether) $C_{23}H_{30}N_4O_4S$ (458.58) Calculated: C 60.24 H 6.59 N 12.22 S 6.99 Found: 60.33 6.62 12.35 7.04

(7) 5E-6-(3-(3-Cyclopentyl-2-phenylsulphonylguanidino)phenyl)-6-(3-pyridyl)hex-5-enoic acid Melting point: 116°–117° C. (ethyl acetate/diiso-propylether) $C_{29}H_{32}N_4O_4S$ (532.66) Calculated: C 65.39 H 6.06 N 10.52 S 6.02 Found: 65.20 6.08 10.39 6.19

Example 10

5E-6-(3-(2-Amidosulphonyl-3-(2-methylpropyl)guanidino)phenyl)-6-(3-pyridyl)hex-5-enoic acid a) Methyl 5E-6-(3-(sulphamoylimido-phenoxymethyleneamino)phenyl)-6-(3 -pyridyl)hex-5-enoate 2.4 g of N-sulphamoyl-diphenyl-imidocarbonate and 3 g of methyl 5E-6-(3-aminophenyl)-6-(3-pyridyl)hex-5-enoate are dissolved in 60 ml of isopropanol and stirred for 36 hours at ambient temperature. The solvent is removed and the residue is purified over a silica gel column with dichloromethane/ethanol=40:1.

Yield: 89% of theory, Oil, $R_f$ value: 0.59 (silica gel; dichloromethane/ethanol=20:1) $C_{25}H_{26}N_4O_5S$ (494.57) Calculated: C 60.71 H 5.30 N 11.33 S 6.48 Found: 60.55 5.43 11.18 6.39 b) 5E-6-(3-(2-Amidosulphonyl-3-(2-methylpropyl)guanidino)phenyl)-6-(3-pyridyl)hex-5-enoic acid 2.2 g of methyl 5E-6-(3-(sulphamoylimidophenoxymethyleneamino)phenyl)-6-(3-pyridyl)hex-5-enoate and 5 ml of 2-methylpropylamine are refluxed for 4 hours in 50 ml of isopropanol. The mixture is cooled to 50° C., combined with 10 ml of 2N sodium hydroxide solution and stirred for 60 minutes at 50° C. The reaction mixture is evaporated down, the residue is taken up in water and extracted with ethyl acetate. The aqueous phase is adjusted to pH 4–5 by the addition of citric acid and extracted with ethyl acetate. The organic extract is evaporated down and the residue is purified over a silica gel column with dichloromethane/ethanol= 30:1. The product fraction is evaporated down and the residue is recrystallised from ethyl acetate/diisopropylether.

Yield: 38% of theory, Melting point: 98° C. (decomp.) $C_{22}H_{29}N_5O_4S$ (459.57) Calculated: C 57.50 H 6.36 N 15.24 S 6.98 Found: 57.62 6.51 15.38 7.05

The following compounds are obtained analogously to Example 10b:

(1) 5E-6-(3-(2-Amidosulphonyl-3-neopentyl-guanidino)phenyl)-6-(3-pyridyl)hex-5-enoic acid Melting point: 136°–140° C. (ethyl acetate/diiso-propylether) $C_{23}H_{31}N_5O_4S$ (473.60) Calculated: C 58.33 H 6.60 N 14.79 S 6.77 Found: 58.28 6.73 14.53 6.50

(2) 5E-6-(3-(2-Amidosulphonyl-3-cyclopentyl-guanidino)phenyl)-6-(3-pyridyl)hex-5-enoic acid. Melting point: 95° C. (decomp., ethyl acetate/diisopropylether) $C_{23}H_{29}N_5O_4S$ (471.58) Calculated: C 58.58 H 6.20 N 14.85 S 6.80 Found: 58.29 6.33 14.65 6.68

Example 11

5E-6-(3-(2-Carbamoyl-2-cyano-1-(2-methylpropylamino)ethyleneamino)phenyl)-6-(3-pyridyl)hex-5-enoic acid 1.5 g of methyl 5E-6-(3-aminophenyl)6-(3-pyridyl)hex-5-enoate and 0.95 g of 1-carbamoyl-1-cyano-2,2-bis(methylthio)ethene are refluxed for 20 hours in 25 ml of isopropanol. The reaction mixture is evaporated down, the oily residue is taken up in 40 ml of isopropanol and combined with 5 ml of 2-methylbutylamine. The reaction mixture is refluxed for 4 hours and then combined with 10 ml of 2N sodium hydroxide solution at 50° C. The reaction solution is stirred for 30 minutes at 50° C. and then evaporated down. The residue is taken up in water and washed with ethyl acetate. The aqueous phase is adjusted to pH 4–5 by the addition of citric acid and extracted with ethyl acetate. The organic extract is dried, evaporated down and the residue is purified over a silica gel column with dichloromethane/ ethanol=30:1.

Yield: 40% of theory, Foam, $R_f$ value: 0.38 (silica gel; dichloromethane/ethanol=20:1) $C_{25}H_{29}N_5O_3$ (447.54) Calculated: C 67.09 H 6.53 N 15.65 Found: 66.94 6.63 15.69

The following compounds are obtained analogously to Example 11:

(1) 5E-6-(3-(2-Carbamoyl-2-cyano-1-cyclopentylaminoethyleneamino)phenyl)-6-(3-pyridyl)hex-5-enoic acid Foam, $R_f$ value: 0.35 (silica gel; dichloromethane/ethanol= 20:1) $C_{26}H_{29}N_5O_3$ (459.55) Calculated: C 67.95 H 6.36 N 15.24 Found: 67.99 6.48 15.06

(2) 5E-6-(3-(2-Carbamoyl-2-cyano-1-propylaminoethyleneamino)phenyl)-6-(3-pyridyl)hex-5-enoic acid Melting point: 161°–163° C. (ethyl acetate/isopropanol) $C_{24}H_{27}N_5O_3$ (433.51) Calculated: C 66.50 H 6.28 N 16.16 Found: 66.37 6.42 16.05

(3) 5E-6-(3-(2-Carbamoyl-2-cyano-1-dimethylaminoethyleneamino)phenyl)-6-(3-Pyridyl)hex-5-enoic acid Foam; $R_f$ value: 0.34 (silica gel; dichloromethane/ethanol=10:1) $C_{23}H_{25}N_5O_3$ (419.50) Calculated: C 65.85 H 6.01 N 16.69 Found: 65.69 6.10 16.54

(4) 5E-6-(3-(2-Cyano-2-methoxycarbonyl-1-(2-methylpropylamino)ethyleneamino)phenyl)-6-(3-pyridyl)-hex-5-enoic acid Prepared analogously to Example 11 by reacting with 1-cyano-1-methoxycarbonyl-2,2-bis(methylthio)ethene. Melting point: 134°–135° C. (ethyl acetate/diisopropylether) $C_{26}H_{30}N_4O_4$ (462.55) Calculated: C 67.51 H 6.54 N 12.11 Found: 67.33 6.48 12.28

(5) 5E-6-(3-(2-Cyano-1-cyclopentylamino-2-methoxycarbonylethyleneamino)phenyl)-6-(3-pyridyl)-hex-5-enoic acid Prepared analogously to Example 11 by reacting with 1-cyano-1-methoxycarbonyl-2,2-bis(methylthio)ethene. Melting point: 150°–151° C. (ethyl acetate/diiso-propylether) $C_{27}H_{30}N_4O_4$ (474.56) Calculated: C 68.34 H 6.37 N 11.81 Found: 68.31 6.46 11.88

Example 12

4E-1-(5-(3-(2-Cyano-3-(2-methylpropyl)guanidino)phenyl)-5-(3-pyridyl)pent-4-enyl)tetrazole 2.25 g of 4E-1-(5-(3-aminophenyl)-5-(3-pyridyl)pent-4-enyl)tetrazole and 2.4 g of diphenoxymethylene-cyanamide are stirred into 50 ml of isopropanol for 20 hours at ambient temperature. The reaction mixture is filtered, the filtrate is combined with 5 ml of 2-methylpropylamine and refluxed for 13 hours. The solvent is removed and the residue is purified over a silica gel column with dichloromethane/methanol/acetic acid=96:4:3.

Yield: 66% of theory, Foam, $R_f$ value: 0.27 (silica gel; dichloromethane/methanol/acetic acid=90:10:3) $C_{23}H_{27}N_9 \times 0.5\ CH_3COOH$ (459.56) Calculated: C 62.73 H 6.36 N 27.43 Found: 62.61 6.52 27.64

The following compound is obtained analogously to Example 12:

(1) 4E-1-(5-(3-(2-Cyano-3-cyclopentyl-guanidino)phenyl)-5-(3-pyridyl)pent-4-enyl)tetrazole Foam, $R_f$ value: 0.07 (silica gel; dichloromethane/ethanol=10:1) $C_{24}H_{27}N_9$ (441.54) Calculated: C 65.29 H 6.16 N 28.55 Found: 65.03 6.28 28.42

Example 13

4E-1-(5-(3-(2,2-Dicyano-1-cyclopentylaminoethylethyleneamino)phenyl)-5-(3-pyridyl)pent-4-enyl)-tetrazole 2.25 g of 4E-1-(5-(3-aminophenyl)-5-(3-pyridyl)pent-4-enyl)tetrazole and 2.15 g of 2,2-dicyano-1,1-bis(methylthio)ethene are refluxed in 50 ml of isopropanol for 48 hours. The reaction mixture is combined with 3 ml of cyclopentylamine and refluxed for a further 26 hours. The solvent is removed and the residue is purified over a silica gel column with dichloromethane/methanol/acetic acid=96:4:3.

Yield: 58% of theory, Foam, $R_f$ value: 0.35 (silica gel RP8; 5% sodium chloride solution/methanol=4:6) $C_{26}H_{27}N_9 \times 0.5\ CH_3COOH$ (495.59) Calculated: C 65.44 H 5.90 N 25.44 Found: 65.26 6.07 25.35

Example 14

5E-6-(3-(2-Benzoyl-3-(2-methylpropyl)guanidino)phenyl)-6-(3-pyridyl)hex-5-enoic acid a) Methyl 5E-6-(3-(benzoylimino-phenoxymethyleneamino)phenyl)-6-(3-pyridyl)hex-5-enoate 5 g of N-benzoyl-diphenylimidocarbonate and 4.14 g of methyl 5E-6-(3-aminophenyl)-6-(3-pyridyl)hex-5-enoate are dissolved in 200 ml of isopropanol and stirred at ambient temperature for 4 hours. The precipitate formed is suction filtered, washed with isopropanol and dried.

Yield: 79% of theory, Melting point: 112° C. $C_{32}H_{29}N_3O_4$ (519.60) Calculated: C 73.97 H 5.63 N 8.09 Found: 73.94 5.68 8.10 b) 5E-6-(3-(2-Benzoyl-3-(2-methylpropyl)guanidino)phenyl)-6-(3-pyridyl)hex-5-enoic acid 2.6 g methyl 5E-6-(3-(benzoylimino-phenoxymethyleneamino)phenyl)-6-(3-pyridyl)hex-5-enoate and 5 ml of 2-methylpropylamine are refluxed for 1 hour in 50 ml of isopropanol. The reaction mixture is cooled to 50° C., mixed with 15 ml of 1N sodium hydroxide solution and stirred for 30 minutes at this temperature. The solvent is removed, the residue is taken up in water and washed with ethyl acetate. The aqueous phase is adjusted to a pH value of 4–5 by the addition of citric acid, the precipitate formed is suction filtered and washed with water. The filter cake is recrystallised from ethyl acetate.

Yield: 74% of theory, Melting point: 159°–160° C. $C_{29}H_{32}N_4O_3$ (484.60) Calculated: C 71.88 H 6.66 N 11.56 Found: 71.92 6.70 11.73

The following compound is obtained analogously to Example 14:

(1) 5E-6-(3-(2-Benzoyl-3-cyclopentyl-guanidino)phenyl)-6-(3-pyridyl)hex-5-enoic acid Melting point: 171° C. (isopropanol/ethyl acetate) $C_{30}H_{32}N_4O_3$ (496.61) Calculated: C 72.56 H 6.50 N 11.28 Found: 72.42 6.55 11.15

Example 15

5E-6-(3-(2-Carbamoyl-3-(2-methylpropyl)guanidino)-phenyl)-6-(3-pyridyl)hex-5-enoic acid 1.34 g of 5E-6-(3-(2-cyano-3-(2-methylpropyl)guanidino)phenyl)-6-(3-pyridyl)hex- 5-enoic acid are dissolved in 50 ml of 4N hydrochloric acid and stirred for 48 hours at ambient temperature. The solution is adjusted to pH 5–6 by the addition of sodium acetate and extracted with ethyl acetate. The organic extract is evaporated down and the residue is purified over a silica gel column with dichloromethane/ethanol=19:1.

Yield: 54% of theory, Foam, $R_f$ value: 0.20 (silica gel; dichloromethane/ethanol=19:1) $C_{23}H_{29}N_5O_3$ (423.52) Calculated: C 65.22 H 6.90 N 16.54 Found: 65.30 7.05 16.37

Example 16

Tablets containing 100 mg of 5E-6-(3-(2,2-dicyano-1-cyclopentylamino-ethyleneamino)phenyl)- 6-(3-pyridyl)-hex-5-enoic acid

| Composition: | |
| --- | --- |
| 1 tablet contains: | |
| Active substance | 100.0 mg |
| Lactose | 80.0 mg |
| Corn starch | 34.0 mg |
| Polyvinylpyrrolidone | 4.0 mg |
| Magnesium stearate | 2.0 mg |
| | 220.0 mg |

Preparation Process

The active substance, lactose and starch are mixed together and uniformly moistened with an aqueous solution of the polyvinylpyrrolidone. After the moist masses have been screened (2.0 mm mesh size) and dried in a rack dryer at 50° C. they are screened again (1.5 mm mesh size) and the lubricant is added. The mixture produced is formed into tablets.

Weight of tablet: 220 mg

Diameter: 9 mm, biplanar, facetted on both sides and notched on one side.

Example 17

Hard gelatin capsules containing 150 mg of 5E-6-(3-(2, 2-dicyano- 1-cyclopentylamino-ethyleneamino)phenyl)-6-(3-pyridyl)-hex-5-enoic acid

| 1 capsule contains: | |
|---|---|
| Active substance | 150.0 mg |
| Dried corn starch about | 180.0 mg |
| Powdered lactose about | 87.0 mg |
| Magnesium stearate | 3.0 mg |
| | about 420.0 mg |

Preparation

The active substance is mixed with the excipients, passed through a 0.75 mm mesh screen and homogeneously mixed in a suitable apparatus.

The final mixture is packed into size 1 hard gelatin capsules.

Capsule contents: about 420 mg

Capsule shell: size 1 hard gelatin capsule.

Example 18

Suppositories containing 150 mg of 5E-6-(3-(2,2-dicyano-1-cyclopentylamino-ethyleneamino)phenyl)- 6-(3-pyridyl)-hex-5-enoic acid

| 1 suppository contains: | |
|---|---|
| Active substance | 150.0 mg |
| Polyethyleneglycol (M.W. 1500) | 550.0 mg |
| Polyethyleneglycol (M.W. 6000) | 460.0 mg |
| Polyoxyethylene sorbitan monostearate | 840.0 mg |
| | 2000.0 mg |

Preparation

After the suppository masses have been melted the active substance is homogeneously distributed therein and the melt is poured into chilled moulds.

Example 19

Suspensions containing 50 mg of 5E-6-(3-(2,2-dicyano-1-cyclopentylamino-ethyleneamino)phenyl)- 6-(3-pyridyl)-hex-5-enoic acid

| 100 ml of suspension contain: | |
|---|---|
| Active substance | 1.0 g |

| 100 ml of suspension contain: | | |
|---|---|---|
| Sodium salt of carboxymethylcellulose | | 0.2 g |
| Methyl p-hydroxybenzoate | | 0.05 g |
| Propyl p-hydroxybenzoate | | 0.01 g |
| Glycerol | | 5.0 g |
| 70% Sorbitol solution | | 50.0 g |
| Flavouring | | 0.3 g |
| Distilled water | ad | 100 ml |

Preparation

Distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the addition of the sorbitol solution and flavouring, the suspension is evacuated to eliminate air, with stirring.

5 ml of suspension contain 50 mg of active substance.

Example 20

Tablets containing 150 mg of 5E-6-(3-(2,2-dicyano-1-cyclopentylamino-ethyleneamino)phenyl)- 6-(3-pyridyl)-hex-5-enoic acid

| Composition: | |
|---|---|
| tablet contains: | |
| Active substance | 150.0 mg |
| Powdered lactose | 89.0 mg |
| Corn starch | 40.0 mg |
| Colloidal silica | 10.0 mg |
| Polyvinylpyrrolidone | 10.0 mg |
| Magnesium stearate | 1.0 mg |
| | 300.0 mg |

Preparation

The active substance mixed with lactose, corn starch and silica is moistened with a 20% aqueous polyvinylpyrrolidone solution and passed through a 1.5 mm mesh screen. The granules dried at 45° C. are rubbed through the same screen again and mixed with the specified amount of magnesium stearate. Tablets are compressed from the mixture.

Weight of tablet: 300 mg

Punch: 10 mm, flat

Example 21

Film-coated tablets containing 75 mg of 5E-6-(3-(2,2-dicyano-1-cyclopentylamino-ethyleneamino)phenyl)-6-(3-pyridyl)-hex-5-enoic acid

| 1 tablet core contains: | |
|---|---|
| Active substance | 75.0 mg |
| Calcium phosphate | 93.0 mg |
| Corn starch | 35.5 mg |
| Polyvinylpyrrolidone | 10.0 mg |
| Hydroxypropylmethylcellulose | 15.0 mg |

-continued

| 1 tablet core contains: | |
|---|---|
| Magnesium stearate | 1.5 mg |
| | 230.0 mg |

Preparation

The active substance is mixed with calcium phosphate, corn starch, polyvinylpyrrolidone, hydroxypropylmethylcellulose and half the specified amount of magnesium stearate. Using a tablet making machine, compressed tablets are produced about 13 mm in diameter which are then rubbed through a 1.5 mm mesh screen on a suitable machine and mixed with the remaining magnesium stearate. These granules are compressed in a tablet making machine to form tablets of the desired shape.

Weight of core: 230 mg
Punch: 9 mm, convex

The tablet cores thus produced are coated with a film consisting essentially of hydroxypropylmethylcellulose. The finished film coated tablets are glazed with beeswax.

Weight of film-coated tablet: 245 mg

Obviously all the other compounds of general formula I may be used as active substances in the galenic preparations described above.

Example 22

Film-coated tablets containing 75 mg of 5E-6-(3-(2,2-dicyano-1-cyclopentylamino-ethyleneamino)phenyl)-6-(3-pyridyl)-hex-5-enoic acid (Substance B)+75 mg of PDE-inhibitor A powdered mixture of

| Dipyridamole | 25% |
|---|---|
| Substance B | 25% |
| Fumaric acid | 15% |
| Cellulose | 20% |
| Corn starch | 8% |
| Polyvinylpyrrolidone | 6% | is moistened with water in a mixing vessel and granulated through a screen with a mesh size of 1.5 mm. After drying and re-screening, 1% magnesium stearate is added and 10 mm biconvex tablets weighing 300 mg are produced. These tablets are sprayed with hydroxypropyl-methylcellulose lacquer until they weigh 312 mg.

Example 23

Hard gelatin capsules, containing 200 mg of 5E-6-(3-(2,2-dicyano-1-cyclopentylamino-ethyleneamino)phenyl)-6-(3-pyridyl)-hex-5-enoic acid (Substance B)+50 mg of PDE-inhibitor 10 kg of dipyridamole, 20 kg of fumaric acid, 11.5 kg of polyvinylpyrrolidone, 40 kg of substance B, 1.5 kg of silicon dioxide and 0.8 kg of magnesium stearate are mixed for 15 minutes in a cube mixer. This mixture is fed through a roller compactor behind which is a dry granulating apparatus with screening means. The fractions measuring 0.25 to 1.0 mm are used. The capsule filling machine is set so that each size 0 capsule contains a quantity of granules corresponding to 50 mg of PDE-inhibitor and 200 mg of substance B.

Example 24

Hard gelatin capsules containing 100 mg of 5E-6-(3-(2,2-dicyano-1-cyclopentylamino-ethyleneamino)phenyl)-6-(3-pyridyl)-hex-5-enoic acid (Substance B)+250 mg of PDE-inhibitor a) Granules 125 kg of mopidamole, 50 kg of fumaric acid and 13.5 kg of lactose are mixed together and moistened with a solution of water/polyethyleneglycol 6000. After granulation through a screen with a mesh size of 1.0 mm and drying at 45° C., 1.4 kg of stearic acid are added.

b) Coated tablets 100 kg of substance B, 7.5 kg of hydroxypropylmethylcellulose, 2.5 kg of silicon dioxide and 15 kg of carboxymethylcellulose are moistened with ethanol and granulated through a screen with a mesh size of 1.5 mm. After drying, 1 kg of magnesium stearate are added and the granules are compressed to form biconvex tablets weighing 126 mg with a diameter of 5.5 mm.

These cores are coated in several steps with a coating suspension consisting of 5.6 kg of saccharose, 0.5 kg of gum arabic and 3.8 kg of talc until the tablets weigh 135 mg.

c) Packaging

The quantity of granules corresponding to 250 mg of PDE-inhibitor are packed into a size 0 long hard gelatin capsule in a special capsule filling machine and the coated tablet containing 100 mg of substance B is placed on top.

Example 25

Suspension containing 10 mg of 5E-6-(3-(2,2-dicyano-1-cyclopentylamino-ethyleneamino)phenyl)-6-(3-pyridyl)-hex-5-enoic acid (Substance B)+100 mg of dipyridamole per 5 g The suspension has the following composition:

| (1) | Dipyridamole | 2.0% |
|---|---|---|
| (2) | Substance B | 0.2% |
| (3) | Sorbitol | 20.8% |
| (4) | Cellulose | 7.5% |
| (5) | Sodium carboxymethylcellulose | 2.5% |
| (6) | Flavour correctors/preservatives | 1.8% |
| (7) | Water | 65.2% |

Ingredients (3)–(6) are stirred into hot water under high shear forces. After cooling, (1), (2) and (7) are incorporated in the viscous suspension.

Example 26

Delayed release preparation containing 50 mg of 5E-6-(3-(2,2-dicyano-1-cyclopentylamino-ethyleneamino)phenyl)-6-(3-pyridyl)-hex-5-enoic acid (Substance B)+200 mg of dipyridamole a) Pellet I A mixture o f

| Substance B | 50.0 kg |
|---|---|
| Lysine | 12.5 kg |
| High polymeric hydroxypropylcellulose | 52.5 kg |
| Triacetine | 4.0 kg |
| Ethyl cellulose | 2.5 kg |
| Magnesium stearate | 3.5 kg | is kneaded with ethanol in a special extruder and extruded in the form of spaghetti (1 mm in diameter) which is rounded off into pellets in a spheronizer. These pellets are then dried thoroughly.

b) Pellet II 300 kg of mixed tartaric acid starter pellets are sprayed in a special container with a suspension consisting of isopropanol, dipyridamole and polyvinyl-pyrrolidone until the pellets of active substance thus produced contain about 45% dipyridamole.

These pellets are sprayed with a lacquer consisting of methacrylic acid/methylmethacrylate copolymer (brand name Eudragit S) and hydroxypropylmethylcellulose-phthalate (brand name HP 55) in a weight ratio of 85:15 to 50:50. The organic lacquer solutions also contain plasticiser and talc. Two pellet components are sprayed with 5 and 7% coating agents and different proportions of the lacquer components within the limits specified. The two components are mixed together so as to give the following in vitro release:

Conditions (corresponding to USPXXI, Basket Method, 100 rpm, 1st hour: artificial gastric juice, pH 1.2, 2nd to 6th hours: artificial intestinal juice (phosphate buffer), pH 5.5):

Release of active substance per hour:

1st hour about 30%

2nd hour about 25%

3rd hour about 18%

4th hour about 12% after the 6th hour more than 90% of the dipyridamole has been released.

c) Packaging

The pellets are mixed together in accordance with the active substance content of pellet components I and II and the desired dosage, and are packed into size 0 long capsules in a capsule filling machine.

Example 27

Ampoules containing 5 mg of 5E-6-(3-(2,2-dicyano-1-cyclopentylamino-ethyleneamino)phenyl)-6-(3-pyridyl)-hex-5-enoic acid (Substance B)+10 mg of dipyridamole per 5 ml Composition:

| (1) | Dipyridamole | 10 mg |
| (2) | Substance B | 5 mg |
| (3) | Propyleneglycol | 50 mg |
| (4) | Polyethyleneglycol | 5 mg |
| (5) | Ethanol | 10 mg |
| (6) | Water for injections ad | 5 ml |
| (7) | 1N HCl ad | pH 3 |

The active substances are dissolved with heating in a solution consisting of ingredients (3)–(7). After the pH has been checked and the mixture filtered sterile, it is poured into suitable ampoules and sterilised.

What is claimed is:

1. A pyridyl derivative of formula

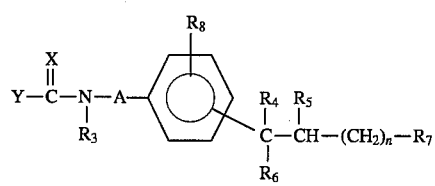

(I)

wherein n represents the number 2, 3, 4 or 5,

A denotes a carbon-nitrogen bond or a straight-chained $C_{1-4}$-alkylene group optionally substituted by one or two alkyl groups, X denotes a nitromethylene group, a cyanomethylene group optionally substituted by an $R_9$ group, or a group of the formula $=N-R_{10}$, wherein $R_9$ denotes a cyano group, an aminocarbonyl group, an alkyl-aminocarbonyl group, a dialkylaminocarbonyl group, a group of the formula

—CO—OR'

—CO—O—(HCR")—O—CO—R''' and

—CO—O—(HCR")—O—CO—OR''' wherein

R' denotes a straight-chained or branched $C_{1-6}$-alkyl group, a $C_{5-7}$-cycloalkyl group, a benzyl, 1-phenylethyl, 2-phenylethyl,' 3-phenylpropyl, methoxymethyl or cinnamyl group, R" denotes a hydrogen atom or a methyl group and R''' denotes a straight-chained or branched $C_{1-6}$-alkyl group, a $C_{5-7}$cycloalkyl group, a phenyl, benzyl, 1-phenylethyl, 2-phenylethyl or 3-phenylpropyl group, or when Y denotes an $R_1NR_2$— group, $R_9$ may also represent a carboxy group, and $R_{10}$ denotes a cyano, alkanesulphonyl, phenylsulphonyl, phenyl-alkanesulphonyl, aminosulphonyl, alkylaminosulphonyl, dialkyl-aminosulphonyl, phenylcarbonyl, aminocarbonyl, alkylaminocarbonyl or dialkylaminocarbonyl group, Y denotes an alkoxy group, a phenoxy group, an alkylthio group, a phenylthio group or a group of the formula —$R_1NR_2$ wherein $R_1$ denotes a hydrogen atom, a straight-chained or branched $C_{1-10}$-alkyl group which may be substituted in the 2-, 3- or 4-position by a hydroxy, amino, alkylamino or dialkylamino group, a $C_{1-4}$-alkyl group which is substituted by a phenyl or pyridyl group and which may additionally be substituted in the 2-, 3- or 4-position by a hydroxy group, a $C_{3-4}$-cycloalkyl group, a $C_{5-8}$-cycloalkyl group in which an ethylene bridge may be re-placed by an o-phenylene group, a $C_{6-8}$-bicycloalkyl group optionally substituted by 1, 2 or 3 alkyl groups, exonorbornyl, adamantyl, alkoxy or trimethylsilylalkyl group, $R_2$ denotes a hydrogen atom, a straight-chained alkyl group or $R_1$ and $R_2$ together with the nitrogen atom between them denote a cyclic $C_{4-6}$-alkyleneimino group which may be substituted by one or two alkyl groups or by a phenyl group, $R_3$ denotes a hydrogen atom or a $C_{1-3}$-alkyl group, $R_4$ and $R_5$ each denote a hydrogen atom or together represent a carbon-carbon bond, $R_6$ denotes a pyridyl group optionally substituted in the 3- or 4-position by an alkyl group, $R_7$ denotes a cyano group, a tetrazolyl group, carboxy, an aminocarbonyl group, an alkylaminocarbonyl group, a dialkylaminocarbonyl group, a group of the formulae

—CO—OR',

—CO—O—(HCR")—O—CO—R''' and

—CO—O—(HCR")—O—CO—OR''' wherein

R' denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R" denotes a hydrogen atom or a methyl group and R''' denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group, or, when Y denotes an $R_1NR_2$— group, $R_7$ may also represent a carboxy group, $R_8$ denotes a hydrogen atom, a fluorine atom, a chlorine atom, a bromine atom, a iodine atom, an alkyl, alkoxy or trifluoromethyl group, whilst all the above-mentioned alkyl and alkoxy moieties, unless otherwise stated, may contain one to three carbon atoms, and all the above-mentioned phenyl nuclei, unless otherwise stated, may be mono- or disubstituted by fluorine, chlorine or bromine atoms or by alkyl, hydroxy, alkoxy, phenyl, nitro, amino, alkylamino, dialkylamino, alkanoylamino, cyano, carboxy, alkoxycarbonyl, aminocarbonyl, alkylaminocarbonyl, di-alkylaminocarbonyl, trifluoromethyl, alkanoyl, aminosulphonyl, alkylaminosulphonyl or dialkylaminosulphonyl groups, and the substituents may be identical or different, the enantiomers thereof, the cis- and trans-isomers thereof, where $R_4$ and $R_5$ together denote a carbon-carbon bond, and the salts thereof.

2. The pyridyl derivative according to claim 1, wherein $R_9$ is a group of formula —CO—OR' wherein R' is a straight chained or branched $C_{1-3}$ alkyl group.

3. The pyridyl derivative of formula I according to claim 1, wherein $R_7$ denotes a carboxy or tetrazolyl group or a group of the formulae

—CO—OR',

—CO—O—(HCR")—O—CO—R''' and

—CO—O—(HCR")—O—CO—OR''' wherein

R' denotes a straight-chained or branched $C_{1-6}$-alkyl group, a $C_{5-7}$-cycloalkyl group, a benzyl, 1-phenylethyl, 2-phenylethyl, 3-phenylpropyl, methoxymethyl or cinnamyl group, R" denotes a hydrogen atom or a methyl group and R''' denotes a straight-chained or branched $C_{1-6}$-alkyl group, a $C_{5-7}$-cycloalkyl group, a phenyl, benzyl, 1-phenylethyl, 2-phenylethyl or 3-phenylpropyl group, the enantiomers thereof, the cis- and transisomers thereof, where $R_4$ and $R_5$ together represent a carbon-carbon bond, and the salts thereof.

4. The pyridyl derivative of formula I according to claim 1, wherein n denotes the number 2, 3, 4 or 5, A is a bond or an ethylene group, X is a nitromethylene group, a cyanomethylene group optionally substituted by an $R_9$ group, or a group of the formula $=N-R_{10}$, wherein $R_9$ denotes a cyano, carboxy, aminocarbonyl, alkylaminocarbonyl, dialkylaminocarbonyl group each having 1 to 3 carbon atoms in the alkyl moieties, or a group of the formula

—CO—OR', wherein

R' denotes a straight-chained or branched $C_{1-3}$-alkyl group and $R_{10}$ denotes a cyano, phenylsulphonyl or alkanesulphonyl group, Y denotes phenoxy or methylthio group or an $R_1NR_2$— group wherein $R_1$ is a hydrogen atom, a straight-chained or branched $C_{1-8}$-alkyl group which may be substituted in the 2-, 3- or 4-position by a hydroxy or dimethylamino group, a $C_{1-4}$-alkyl group which is substituted by a phenyl or pyridyl group and may additionally be substituted in the 2-, 3- or 4-position by a hydroxy group, a $C_{3-8}$-cycloalkyl group, a methoxy, trimethylsilylmethyl or indan-2-yl group or a bicycloheptyl group optionally substituted by 1, 2 or 3 alkyl groups and $R_2$ is a hydrogen atom or a methyl group or $R_1$ and $R_2$ together with the nitrogen atom between them denote a piperidino group which may be substituted by one or two methyl groups or by a phenyl group, $R_3$ denotes a hydrogen atom or a methyl group, $R_4$ and $R_5$ each denote a hydrogen atom or together represent another carbon-carbon bond, $R_6$ denotes a 3-pyridyl or 4-pyridyl group and $R_7$ denotes a cyano, carboxy, tetrazolyl, aminocarbonyl, alkyl-aminocarbonyl, dialkylaminocarbonyl group each having 1 to 3 carbon atoms in the alkyl moieties, or a group of the formula

—CO—OR', wherein

R' denotes a straight-chained or branched $C_{1-3}$-alkyl group, $R_8$ denotes a hydrogen, fluorine, chlorine or bromine atom or an alkyl, alkoxy or trifluoromethyl group, whilst unless otherwise stated all the above-mentioned alkyl and alkoxy moieties may contain one to three carbon atoms, the enantiomers thereof, the cis- and trans-isomers thereof, where $R_4$ and $R_5$ together denote a carbon-carbon bond, and the salts thereof.

5. The pyridyl derivative of formula I according to claim 1, wherein n denotes the number 3, A denotes a bond or an ethylene group, X denotes a dicyanomethylene group or a group of the formula $=N-R_{10}$ wherein $R_{10}$ is a cyano or phenylsulphonyl group, Y is an $R_1NR_2$— group, wherein $R_1$ is a straight-chained or branched $C_{1-8}$-alkyl group, a $C_{3-8}$-cycloalkyl group or an exonorbornyl-(2) group and $R_2$ is a hydrogen atom, $R_3$ is a hydrogen atom, $R_4$ and $R_5$ each represent a hydrogen atom or together denote a carbon-carbon bond, $R_6$ is a 3-pyridyl group and $R_7$ denotes a carboxy group or a group of the formula

—CO—OR', wherein

R' denotes a straight-chained or branched $C_{1-3}$-alkyl group, $R_8$ is a hydrogen, chlorine or bromine atom or a methyl or tri-fluoromethyl group, the enantiomers thereof, the cis- and trans-isomers thereof, where $R_4$ and $R_5$ together denote a carbon-carbon bond, and the salts thereof.

6. The pyridyl derivative according to claim 1, 5E-6-(3-(2-cyano-3-cyclopropyl-guanidino)phenyl)-6-(3-pyridyl)hex-5-enoic acid, and the cis- and trans isomers thereof and the salts thereof.

7. The pyridyl derivative according to claim 1, 5E-6-(3-(2-cyano-3-tert.butyl-guanidino)phenyl)-6-(3-pyridyl)hex-5-enoic acid, and the cis- and trans isomers thereof and the salts thereof.

8. The pyridyl derivative according to claim 1, 5E-6-(3-(2-cyano-3-cyclopentyl-guanidino)phenyl)-6-(3-pyridyl)hex-5-enoic acid, and the cis- and trans isomers thereof and the salts thereof.

9. The pyridyl derivative according to claim 1, 5E-6-(3-(2-cyano-3-isopropyl-guanidino)phenyl)-6-(3-pyridyl)hex-5-enoic acid, and the cis- and trans isomers thereof and the salts thereof.

10. The pyridyl derivative according to claim 1, 5E-6-(3-(2-cyano-3-(exo-norborn-2-yl)guanidino)-phenyl-6 -(3-pyridyl)hex-5-enoic acid, and the cis- and trans iosmers thereof and the salts thereof.

11. The pyridyl derivative according to claim 1, 5E-6-(3-(2-cyano-3-(2-methylpropyl)guanidino)phenyl)-6-(3-pyridyl)hex-5-enoic acid, and the cis- and trans isomers thereof and the salts thereof.

12. The pyridyl derivative according to claim 1, 5E-6-(3-(2-cyano-3-neopentyl-guanidino)phenyl)-6-(3-pyridyl)hex-5-enoic acid, and the cis- and trans isomers thereof and the salts thereof.

13. The pyridyl derivative according to claim 1, 5E-6-(3-(2-cyano-3-pentyl-guanidino)phenyl)-6-(3-pyridyl)hex-5-enoic acid, and the cis- and trans isomers thereof and the salts thereof.

14. The pyridyl derivative according to claim 1, 5E-6-(3-(2-cyano-3-(3-methylbutyl)guanidino)phenyl)-6-(3-pyridyl)hex-5-enoic acid, and the cis- and trans isomers thereof and the salts thereof.

15. The pyridyl derivative according to claim 1, 5E-6-(3-(2,2-dicyano-1-(2-methylpropylamino)ethyleneamino)phenyl)-6-(3-pyridyl)hex-5-enoic acid, and the cis- and trans isomers thereof and the salts thereof.

16. The pyridyl derivative according to claim 1, 5E-6-(3-(2,2-dicyano-1-isopropylamino-ethyleneamino)phenyl)-6-(3-pyridyl)hex-5-enoic acid, and the cis- and trans isomers thereof and the salts thereof.

17. The pyridyl derivative according to claim 1, 5E-6-(3-(2,2-dicyano-1-(3-methylbutylamino)-ethyleneamino)phenyl)-6-(3-pyridyl)hex-5-enoic acid, and the cis- and trans isomers thereof and the salts thereof.

18. The pyridyl derivative according to claim 1, 5E-6-(3-(2,2-dicyano-1-cyclopentylamino-ethyleneamino)phenyl)-6-(3-pyridyl)hex-5-enoic acid, and the cis- and trans isomers thereof and the salts thereof.

19. The pyridyl derivative according to claim 1, 5E-6-(3-(2,2-dicyano-1-neopentylamino-ethyleneamino)phenyl)-6-(3-pyridyl)hex-5-enoic acid, and the cis- and trans isomers thereof and the salts thereof.

20. The pyridyl derivative according to claim 1, 5E-6-(3-(2,2-dicyano-1-cyclopropylamino-ethyleneamino)-phenyl)-6-(3-pyridyl)hex-5-enoic acid, and the cis- and trans isomers thereof and the salts thereof.

21. The pyridyl derivative according to claim 1, 5E-6-(3-(2,2-dicyano-1-propylamino-ethyleneamino)-phenyl)-6-(3-pyridyl)hex-5-enoic acid, and the cis- and trans isomers thereof and the salts thereof.

22. The pyridyl derivative according to claim 1, 5E-6-(3-(2,2-dicyano-1-tert.butylamino-ethyleneamino)phenyl)-6-(3-pyridyl)hex-5-enoic acid, and the cis- and trans isomers thereof and the salts thereof.

23. The pyridyl derivative according to claim 1, 5E-6-(4-(2-cyano-3-cyclohexyl-guanidino)phenyl)-6-(3-pyridyl)hex-5-enoic acid, and the cis- and trans isomers thereof and the salts thereof.

24. The pyridyl derivative according to claim 1, 6-(3-(2-cyano-3-tert.butyl-guanidino)phenyl)-6-(3-pyridyl)hexanoic acid, and the cis- and trans isomers thereof and the salts thereof.

25. The pyridyl derivative according to claim 1, 5E-6-(3-(1-neopentylamino-2-nitro-ethyleneamino)-phenyl)-6-(3-pyridyl)hex-5-enoic acid, and the cis- and trans isomers thereof and the salts thereof.

26. The pyridyl derivative according to claim 1, E/Z-6-(4-(2-(2-cyano-3-tert.butyl-guanidino)ethyl)- phenyl)-6-(3-pyridyl)hex-5-enoic acid, and the cis- and trans isomers thereof and the salts thereof.

27. The pyridyl derivative according to claim 1, 5E-6-(3-(3-tert.butyl-2-phenylsulphonyl-guanidino)phenyl)-6-(3-pyridyl)hex-5-enoic acid, and the cis- and trans isomers thereof and the salts thereof.

28. The pyridyl derivative according to claim 1, 5E-6-(3-(2-amidosulphonyl-3-(2-methylpropyl)-guanidino)phenyl)-6-(3-pyridyl)hex-5-enoic acid, and the cis- and trans isomers thereof and the salts thereof.

29. The pyridyl derivative according to claim 1, 5E-6-(3-(2-carbamoyl-2-cyano-1-(2-methylpropylamino)ethyleneamino)phenyl)-6-(3-pyridyl)hex-5-enoic acid, and the cis- and trans isomers thereof and the salts thereof.

30. The pyridyl derivative according to claim 1, 4E-1-(5-(3-(2-cyano-3-cyclopentyl-guanidino)-phenyl)-5-(3-pyridyl)pent-4-enyl)tetrazole, and the cis- and trans isomers thereof and the salts thereof.

31. 5E-6-(3-(2,2-Dicyano-1-cyclopentylaminoethyleneamino)phenyl)-6-(3-pyridyl)hex-5-enoic acid, the cis- and trans-isomers thereof and the salts thereof.

32. Physiologically acceptable salt of the pyridyl derivative according to claim 1 with inorganic or organic acids or bases.

33. Pharmaceutical composition comprising as active substance a pyridyl derivative according to claim 1 together with one or more inert carriers or diluents.

34. A method of treating thromboembolic disorders in a warm-blooded animal which comprises administering to said animal a therapeutically effective amount of a pyridyl derivative according to claim 1.

35. A method of preventing thromboemobolic disorders in a warm-blooded animal in need thereof which comprises administering to said animal a therapeutically effective amount of a pyridyl derivative according to claim 1.

36. A method for prophylaxis of arteriosclerosis in a warm-blooded animal in need thereof which comprises administering to said animal a therapeutically effective amount of a pyridyl derivative according to claim 1.

37. A method for treating ischaemia in a warm-blooded animal which comprises administering to said animal a therapeutically effective amount of a pyridyl derivative according to claim 1.

38. A method for treating asthma in a warm-blooded animal which comprises administering to said animal a therapeutically effective amount of a pyridyl derivative according to claim 1.

39. A method for treating allergy in a warm-blooded animal which comprises administering to said animal a therapeutically effective amount of a pyridyl derivative according to claim 1.

40. A method for treating or preventing diseases in a warm-blooded animal in need thereof in which thromboxane-mediated constriction of capillaries is involved which comprises administering to said animal a therapeutically effective amount of a pyridyl derivative according to claim 1.

41. A method for treating or preventing diseases in a warm-blooded animal in need thereof in which $PGE_2$-mediated dilation of capillaries is involved which comprises administering to said animal a therapeutically effective amount of a pyridyl derivative according to claim 1.

42. A method for reducing severity of transplant rejection in a warm-blooded animal which comprises administering to said animal a therapeutically effective amount of a pyridyl derivative according to claim 1.

43. A method for reducing renal toxicity of immunosuppressant substances in a warm-blooded animal which comprises administering to said animal a therapeutically effective amount of a pyridyl derivative according to claim 1.

44. A method for treating kidney diseases in a warm-blooded animal in need thereof which comprises administering to said animal a therapeutically effective amount of a pyridyl derivative according to claim 1.

45. A method for treating shock in a warm-blooded animal which comprises administering to said animal a therapeutically effective amount of a pyridyl derivative according to claim 1.

* * * * *